United States Patent
Mithen

(10) Patent No.: US 11,147,825 B2
(45) Date of Patent: Oct. 19, 2021

(54) GLUCORAPHNIN FOR USE IN THE TREATMENT AND/OR PREVENTION OF DIABETES MELLITUS

(71) Applicant: PLANT BIOSCIENCE LIMITED, Norwich (GB)

(72) Inventor: Richard Mithen, Norwich (GB)

(73) Assignee: Plant Bioscience Limited, Norwich (GB)

(*) Notice: Subject to any disclaimer, the term of this patent is extended or adjusted under 35 U.S.C. 154(b) by 103 days.

(21) Appl. No.: 15/738,660

(22) PCT Filed: Jun. 24, 2016

(86) PCT No.: PCT/GB2016/051898
§ 371 (c)(1),
(2) Date: Dec. 21, 2017

(87) PCT Pub. No.: WO2016/207651
PCT Pub. Date: Dec. 29, 2016

(65) Prior Publication Data
US 2018/0177811 A1 Jun. 28, 2018

Related U.S. Application Data

(60) Provisional application No. 62/185,379, filed on Jun. 26, 2015.

(51) Int. Cl.
| A61K 36/31 | (2006.01) |
| A61K 31/7028 | (2006.01) |
| A23L 33/105 | (2016.01) |
| A23L 23/00 | (2016.01) |
| A23L 19/00 | (2016.01) |
| A61P 3/10 | (2006.01) |

(52) U.S. Cl.
CPC .......... *A61K 31/7028* (2013.01); *A23L 19/03* (2016.08); *A23L 23/00* (2016.08); *A23L 33/105* (2016.08); *A61K 36/31* (2013.01); *A61P 3/10* (2018.01); *A23V 2002/00* (2013.01)

(58) Field of Classification Search
None
See application file for complete search history.

(56) References Cited

U.S. PATENT DOCUMENTS

| 2008/0131578 A1* | 6/2008 | Caudill ..................... A23L 2/52 426/589 |
| 2014/0075590 A1 | 3/2014 | Van Den Bosch et al. |
| 2014/0189905 A1 | 7/2014 | Mithen et al. |

FOREIGN PATENT DOCUMENTS

| CN | 104434941 A | 3/2015 |
| EP | 2708115 A1 | 3/2014 |
| EP | 2708607 A2 | 3/2014 |
| JP | 2008-303154 A | 12/2008 |
| JP | 2014-064567 A | 4/2014 |
| JP | 2014-076045 A | 5/2014 |
| KR | 20120054946 A | 5/2012 |
| WO | WO-99/52345 A1 | 10/1999 |
| WO | WO-2010/001119 A2 | 1/2010 |
| WO | WO-2011/077163 A2 | 6/2011 |
| WO | WO-2014/008361 A2 | 1/2014 |

OTHER PUBLICATIONS

Conzatti et al. ("Clinical and molecular evidence of the consumption of broccoli, glucoraphanin and sulforaphane in humans", Nutricion Hospital Alaria 2015, vol. 31, No. 2, 2015, pp. 559-569, XP055301464, ISSN: 1699-5198), document is provided within the IDS (Year: 2015).*
Database WPI (Week 201270, Thomson Scientific, London, GB; AN 2012-G40252 & KR 2012 0054946 A (Univ Konkuk Ind Coop Corp) May 31, 2012 (May 31, 2012), p. 1, document is provided within the IDS (Year: 2012).*
Berhow et al., Purification of a Sinapine-Glucoraphanin Salt from Broccoli Seeds, Am. J. Plant Sci., 1(2):113-8 (Dec. 2010).
Conzatti et al., Clinical and molecular evidence of the consumption of broccoli, glucoraphanin and sulforaphane in humans, Nutr. Hosp., 31(2):559-69 (Nov. 2014).
Database WPI Week 201270, Thomson Scientific, London, Great Britain, AN 2012-G40252 (May 31, 2012).
Gasper et al., Glutathione S-transferase M1 polymorphism and metabolism of sulforaphane from standard and high-glucosinolate broccoli, Am. J. Clin. Nutr., 82(6):1283-91 (Dec. 2005).
International Application No. PCT/GB2016/051898, International Search Report and Written Opinion, dated Sep. 27, 2016.
Lee et al., Extraction and Purification of Glucoraphanin by Preparative High-Performance Liquid Chromatography (HPLC), J. Chem. Educ., 88(6):832-4 (2011).
Ravikumar, Therapeutic Potential of *Brassica oleracea* (Broccoli)—A Review, Int. J. Drug Dev. & Res., 7:2 (2015).

(Continued)

Primary Examiner — Michael Barker
Assistant Examiner — Randall O Winston
(74) Attorney, Agent, or Firm — Marshall, Gerstein & Borun LLP

(57) ABSTRACT

A composition comprising glucoraphanin for use in: reducing fasting serum glucose levels in a subject administered with said composition when compared to a subject not administered said composition; and/or preventing diabetes mellitus and/or a condition associated therewith, treating diabetes mellitus and/or a condition associated therewith, or a combination thereof in a subject; wherein the composition is intermittently administered to the subject between about 1 to about 5 times per week such that said subject is administered with a weekly dose of between about 300 to about 2500 μmoles of glucoraphanin, as well as uses of a composition prepared from a high glucosinolate broccoli and/or methods of: reducing fasting serum glucose levels in a subject having elevated fasting serum glucose levels; preventing diabetes mellitus and/or a condition associated therewith in a subject; treating a subject having diabetes mellitus and/or a condition associated therewith; or combinations thereof.

14 Claims, 3 Drawing Sheets

Specification includes a Sequence Listing.

(56) References Cited

OTHER PUBLICATIONS

Bahadoran et al., Broccoli sprouts powder could improve serum triglyceride and oxidized LDL/LDL-cholesterol ratio in type 2 diabetic patients: a randomized double-blind placebo-controlled clinical trial, Diabetes Res. Clin. Practice, 96:348-54 (2012).

Bahadoran et al., Effects of broccoli sprouts on insulin resistance in type 2 diabetic patients: a randomized double-blind clinical trial, Int. J. Food Sci. Nutrition, 63(7):767-771 (Nov. 2012).

Mirmiran et al., Effects of broccoli sprout with high sulforaphane concentration on imflammatory markers in type 2 diabetic patients: a randomized double-blind placebo-controlled clinical trial, J. Functional Foods, 4:837-41 (2012).

Mithen et al., Human dietary intervention study to investigate the effect of sulforaphane on prostate cancer interception, Protocol Version 7, Norfolk and Norwich University Hospitals, Annex 1—study protocol Mar. 16, 2015.

Nagata N et al., Glucoraphanin Ameliorates Obesity and Insulin Resistance Through Adipose Tissue Browning and Reduction of Metabolic Endotoxemia in Mice, Diabetes, 2017, vol. 66(5), pp. 1222-1236.

\* cited by examiner

FIGURE 1

The *B.oleracea* lines sequenced to create this consensus are:
GD33
breeder line 560216
breeder ID field number 2153.

The lines that contain the FT69 allele and were used to create this consensus are:
Breeder line 560526
Breeder line 580333
Breeder line BRM 51-1162
Breeder line BRM51-1210

```
FT69        1    GAAAATCACAGTTCACGCCTCTTACTCCATGAGCTTCTCTATTCTCATCC
Oleracea    1    GAAAATCACAGTTCACGCCTCTTACTCCATGAGCTTCTCTATTCTCATCC FT69        51   TAGTGTTATAATCTTGCAAACACATATAGAAAGCAAGATTTGGAGTGTAC
Oleracea    51   TAGTGTTATAATCTTGCAAACACATATAGAAAGCAAGGTTTGGAGTGTAC FT69        101  GAGAAAAACATGAAAACACCTAGAAGCTCTGTGGGTAAGACCCAAGAGCG
Oleracea    101  GAGAAAAACATGAAAACACCTAGAAGCTCTGTGGGTGAGACCCAAGAGCG FT69        151  TTTCTCGATTAGTTTCATATACAGATGCATCAGAGTTCTCATCAACCGAT
Oleracea    151  TTTCTCGATTAGTTTCATATACAGATGCATCAGAGTTCTCATCAACCGAT FT69        201  CTACTTCTTTCTTATCTTATTAGAAAAAAAAAATCCTATCAAAATTTACT
Oleracea    201  CTACTTCTTTCTTATCTTATTAGAAGAAAAAAATCCTATCAAAATTTACT FT69        251  TTCCTGCAAGTATATTTTCTTTACATTTTCATTTTCTTGAGTGTTATTT
Oleracea    251  TTCCTGCAAGTATATTTTCTTTACATTTTCATTTTCTTGAGTGTTATTT FT69        301  GAGTGAAGTTATATTAAAATATT........GTTCATATATATCGAAAAT
Oleracea    301  GAGTGAAGTTATATTAAAATATTGTAATAGAGTTCATATATATCGAAAAT FT69        351  GTCAAGAAAGCCATGTTGTGTCGGAGAAGGGCTGAAGAAAGGGGCATGGA
Oleracea    351  GTCAAGAAAGCCATGTTGTGTCGGAGAAGGGCTGAAGAAAGGGGCATGGA FT69        401  CCACCGAGGAAGATAAGAAACTCATCTCTTACATCCATGAACATGGAGAA
Oleracea    401  CCACCGAGGAAGATAAGAAACTCATCTCTTACATCCATGAACATGGAGAA FT69        451  GGAGGCTGGCGCGACATTCCTCAAAAAGCTGGTTAATATCTATTATATAT
Oleracea    451  GGAGGCTGGCGCGACATTCCTCAAAAAGCTGGTTAATATCTATTATATAT FT69        501  TTTTTGGTAAATTTTTAAAAC..ATATATGTTTGTTTGGTATTTGATGTA
Oleracea    501  TTTTTGGTAAATTTTTAAAACATATATATGTTTGTTTGGTATTTGATGTA FT69        551  TGAAAGTTTTATATTGAATGTGGTGTTTTACTAGGATTGAAAAGGTGTGG
Oleracea    551  TGAAAGTTTTATGTTGAATATGGTGTTTTACTAGGRTTGAAAAGGTGTGG FT69        601  AAAGAGTTGCAGACTGCGATGGACTAACTACCTAAAACCTGAGATCAAAA
Oleracea    601  AAAGAGTTGTAGACTGCGATGGACTAACTACCTAAAACCTGAGATCAAAA FT69        651  GAGGCGAGTTTAGTTCAGAGGAGGAACAGATTATCATCATGCTCCATGCT
Oleracea    651  GAGGCGAGTTTAGTTCAGAGGAGGAACAGATTATCATCATGCTCCATGCT FT69        701  GCTCGTGGCAACAAGTACGTTTATTTTAGACCAAAAAAAAACAAGTACGT
Oleracea    701  GCTCGTGGCAACAAGTACGTTTATTTTAGACCAAAAAAAAACAAGTACGT FT69        751  TTATTTTTAACAAAAAGGACGATTATATATTTT..TGTGTGTATGGATCC
Oleracea    751  TTATTTTTAACAAAAAGGACGATTATATATTTTTATGTGTGTATGGATCC FT69        801  TCCAGTGATCATCATTCTAGTTTTCTCTTCTTTTTTTTATACCGCAAACA
Oleracea    801  TCCAGTGATCATCATTCTAGTTTTCTCTTTTTTTTT..ATACCGCAAACA FT69        851  AATTTCATTAGTAAAAAAATTAAAATTCCAAAGTCAATATTCAAAAACA
Oleracea    851  AATTTCATTAGTAAAAAAA.TTAAAATTCCAAAGTCAATATTCAAAAACA FT69        901  CAGTGTTATATA....ATCCTATATATGTCATATATTAAAAAAGTATATT
Oleracea    901  CAGTGTTATATATATAATCCTATATATGTCATATATTAAAAAAGTA....

FT69        951  AAAAAAGTACAACATGAGAAATGAATTTAAGTATGCTTCTAAAGCGAAGT
Oleracea    951  ..........CAACATGAGAAATGAATTTAAGTATGCTTCTAAAGCGAAGT
```

FIGURE 1 Continued

```
FT69     1001 TTTACTTCCCAAAAAATTATTCTTTATTTTTTTCATGTATTTGACAATTC
Oleracea 1001 TTTACTTCCCGAAAAATTATTCTTTATTTTTTTCATGTATTTGACAATTC FT69     1051 TCTGATGCAAAATATGTGTTTGATTAGCAATATGTGACTAAAAATTGCAA
Oleracea 1051 TCTGATGCAAAATATGTGTTTGATTAGCAATATGTGACTAAAAATTGCAA FT69     1101 TAGCACACATCATTTTAGTCTCTATTCCATAGAAAAGCTTCAAAATAAAT
Oleracea 1101 TAGCACACATCATTTTAGTCTCTATTCCATAAAAAAGCTTCAAAATAAAT FT69     1151 TTGATTAACTTTGGTCTTCCATCTTATCTCTTTCACTATTCTTGTCTTTA
Oleracea 1151 TTGATTAACTTTGGTCTTCCATCTTATCTCTTTCACTATTCTTGTCTTTA FT69     1201 GGTGGTCGGTCATAGCKAGACATTTACCTAGAAGAACMGACAATGAGATC
Oleracea 1201 GGTGGTCGGTCATAGCKAGACATTTACCTAGAAGAACMGACAATGAGATC FT69     1251 AAGAAYTACTGGAACACACATCTCAAGAAACGTTTGATCGAACAGGGTAC
Oleracea 1251 AAGAACTACTGGAACACACATCTCAAGAAACGTTTGATCGAACAGGGTAC FT69     1301 TGATCCCGTGACTCACAAGCCACTAGCTTCTAATACAAACCCTACTGTAC
Oleracea 1301 TGATCCCGTGACTCACAAGCCACTAGCTTCTAATACAAACCCTACTGTAC FT69     1351 CTGAGAATTTGCATTCCCTAGATGCATCTAG   TTCCGACAAGCAATAC
Oleracea 1351 CTGAGAATTTGCATTCCCTAGATGCATCTAGTAATTCCGACAAGCAATAC FT69     1401 TCCCGGTCAAGCTCAATGCCTTCCATGTCTTGTACTCCTTCCTCCGGTTT
Oleracea 1401 TCCCGGTCAAGCTCAATGCCTTCCATGTCTTGTACTCCTTCCTCCGGTTT FT69     1451 CAACACGGTTTTCGAGAATACCAGCAAAGATGGGACACCAGTTCGTGAGG
Oleracea 1451 CAACACGGTTTTCGAGAATACCAGCAAAGATGGGACACCAGTTCGTGAGG FT69     1501 ACGATTCCTTGAGTCGCAAGAAACGTTTGAAGAAATCAAGTTCTACATCA
Oleracea 1501 ACGATTCCTTGAGTCGCAAGAAACGTTTTAAGAAATCAAGTTCTACATCA FT69     1551 AGGCTTTTGAACAAAGTTGCGGCTAAGGCCACTTCCATGAAAAAAGCTTT
Oleracea 1551 AGGCTTTTGAACAAAGTTGCGGCTAAGGCCACTTCCATGAAAGAAGCTTT FT69     1601 GTCTGCTTCCATGGAAGGTAGCTTGAATGCTAATATAAGCTTTTCCAATG
Oleracea 1601 GTCTGCTTCCATGGAAGGTAGTTTGAATGCTAATACAAGCTTTTCCAATG FT69     1651 GCTACTCTGAGCAGATTCTCAATGAAGATGATAGTTCTAATGCATCCCTC
Oleracea 1651 GCTACTCTGAGCAGATTCTCAATGAAGATGATAGTTCTAATGCATCCCTC FT69     1701 ATAAACACTCTCGCCGAGTTCGATCCCTTCCTCCAAACAACGTTTTACCC
Oleracea 1701 ATAAACACTCTCGCCGAGTTCGATCCCTTCCTCCAAACAACGTTTTACCC FT69     1751 TGAGAATGAGATGAATACTACTTCTGATCTCGGTATAGATCAGGACTACT
Oleracea 1751 TGAGAATGAGATGAATACTACTTCTGATCTCGGTATAGATCAGGACTACT FT69     1801 TCTCACATTTTCTCGAAAATTTCGGCA          ACCATAATGAGGAG
Oleracea 1801 TCTCACATTTTCTCGAAAATTTCGGCAGAGATGATGACCACAATGAGGAG FT69     1851 CACTACATGAATCATAACTATGGTCATGGTCTTCTTATGTCCTATGTGTC
Oleracea 1851 CACTACATGAATCATAACTATGGTCATGATCTTCTTATGTCCGATGTGTC FT69     1901 CCAAGAAGTCTCATCAACTAGCGTTGATGATCAAGACAATACTAATGAGG
Oleracea 1901 CCAAGAAGTCTCATCAACTAGCGTTGATGATCAAGACAATACTAATGAGG FT69     1951 GTTGGTCAAATTATCTTCTTGACCATGCTGATTTTATACATGACATGGAT
Oleracea 1951 GTTGGTCAAATTATCTTCTTGACCATGCTGATTTTATACATGACATGGAT FT69     2001 TCTGATTCCCTCGGAAAGCATCTCATATGAATCTTCGTGCCTAAGCAGAA
Oleracea 2001 TCTGATTCCCTCGGAAAGCATCTCATATGAATCTTCGTGCCCAAGCAGAA FT69     2051 AGGTTTCAAACT          TGTCAGAACAAGAAGTTATGTATGTATTC
Oleracea 2051 AGGTTTCAAACTTTTGAAACTTGTCAGAACAAGAAGTTATGTATGTATTC FT69     2101 TATTATATGGATTGTTTAGTATATGTCCAAGATCATGGTTGTTAGTCCCA
Oleracea 2101 TATTATATGGATTGTTTAGTATATGTCCAAGATCATGGTTGTTAGTCCCA FT69     2151 AGTTTAGGGTTTGTATAATATACAATAAGGGACGTTATCTTATAAAACGA
Oleracea 2151 AGTTTAGGGTTTGTATAATATACAATAAGGGACGTTATCTTATAAAACGA
```

FIGURE 1 Continued

```
FT69     2201 GG
Oleracea 2201 GG
```

FIGURE 2

(SEQ ID No. 1)

*Brassica oleracea Myb28*

```
1    GAAAATCACAGTTCACGCCTCTTACTCCATGAGCTTCTCTATTCTCATCC
51   TAGTGTTATAATCTTGCAAACACATATAGAAAGCAAGGTTTGGAGTGTAC
101  GAGAAAAACATGAAAACACCTAGAAGCTCTGTGGGTGAGACCCAAGAGCG
151  TTTCTCGATTAGTTTCATATACAGATGCATCAGAGTTCTCATCAACCGAT
201  CTACTTCTTTCTTATCTTATTAGAAGAAAAAAATCCTATCAAAATTTACT
251  TTCCTGCAAGTATATTTTTCTTTACATTTTCATTTTCTTGAGTGTTATTT
301  GAGTGAAGTTATATTAAAATATTGTAATAGAGTTCATATATATCGAAAAT
351  GTCAAGAAAGCCATGTTGTGTCGGAGAAGGGCTGAAGAAGGGGCATGGA
401  CCACCGAGGAAGATAAGAAACTCATCTCTTACATCCATGAACATGGAGAA
451  GGAGGCTGGCGCGACATTCCTCAAAAAGCTGGTTAATATCTATTATATAT
501  TTTTTGGTAAATTTTTAAAACATATATATGTTTGTTTGGTATTTGATGTA
551  TGAAAGTTTTATGTTGAATATGGTGTTTTACTAGGRTTGAAAAGGTGTGG
601  AAAGAGTTGTAGACTGCGATGGACTAACTACCTAAAACCTGAGATCAAAA
651  GAGGCGAGTTTAGTTCAGAGGAGGAACAGATTATCATCATGCTCCATGCT
701  GCTCGTGGCAACAAGTACGTTTATTTTAGACCAAAAAAAAACAAGTACGT
751  TTATTTTTAACAAAAAGGACGATTATATATTTTTATGTGTGTATGGATCC
801  TCCAGTGATCATCATTCTAGTTTTCTCTTTTTTTTTATACCGCAAACAAA
851  TTTCATTAGTAAAAAAATTAAAATTCCAAAGTCAATATTCAAAAACACAG
901  TGTTATATATATAATCCTATATATGTCATATATTAAAAAAGTACAACATG
951  AGAAATGAATTTAAGTATGCTTCTAAAGCGAAGTTTTACTTCCCGAAAAA
1001 TTATTCTTTATTTTTTTCATGTATTTGACAATTCTCTGATGCAAAATATG
1051 TGTTTGATTAGCAATATGTGACTAAAAATTGCAATAGCACACATCATTTT
1101 AGTCTCTATTCCATAAAAAAGCTTCAAAATAAATTTGATTAACTTTGGTC
1151 TTCCATCTTATCTCTTTCACTATTCTTGTCTTTAGGTGGTCGGTCATAGC
1201 KAGACATTTACCTAGAAGAACMGACAATGAGATCAAGAACTACTGGAACA
1251 CACATCTCAAGAAACGTTTGATCGAACAGGGTACTGATCCCGTGACTCAC
1301 AAGCCACTAGCTTCTAATACAAACCCTACTGTACCTGAGAATTTGCATTC
1351 CCTAGATGCATCTAGTAATTCCGACAAGCAATACTCCCGGTCAAGCTCAA
1401 TGCCTTCCATGTCTTGTACTCCTTCCTCCGGTTTCAACACGGTTTCGAG
1451 AATACCAGCAAAGATGGGACACCAGTTCGTGAGGACGATTCCTTGAGTCG
1501 CAAGAAACGTTTTAAGAAATCAAGTTCTACATCAAGGCTTTTGAACAAAG
1551 TTGCGGCTAAGGCCACTTCCATGAAAGAAGCTTTGTCTGCTTCCATGGAA
1601 GGTAGTTTGAATGCTAATACAAGCTTTTCCAATGGCTACTCTGAGCAGAT
1651 TCTCAATGAAGATGATAGTTCTAATGCATCCCTCATAAACACTCTCGCCG
1701 AGTTCGATCCCTTCCTCCAAACAACGTTTTACCCTGAGAATGAGATGAAT
1751 ACTACTTCTGATCTCGGTATAGATCAGGACTACTTCTCACATTTTCTCGA
1801 AAATTTCGGCAGAGATGATGACCACAATGAGGAGCACTACATGAATCATA
1851 ACTATGGTCATGATCTTCTTATGTCCGATGTGTCCCAAGAAGTCTCATCA
1901 ACTAGCGTTGATGATCAAGACAATACTAATGAGGGTTGGTCAAATTATCT
1951 TCTTGACCATGCTGATTTTATACATGACATGGATTCTGATTCCCTCGGAA
2001 AGCATCTCATATGAATCTTCGTGCCCAAGCAGAAAGGTTTCAAACTTTTG
2051 AAACTTGTCAGAACAAGAAGTTATGTATGTATTCTATTATATGGATTGTT
2101 TAGTATATGTCCAAGATCATGGTTGTTAGTCCCAAGTTTAGGGTTTGTAT
2151 AATATACAATAAGGGACGTTATCTTATAAAACGAGG
```

GLUCORAPHNIN FOR USE IN THE TREATMENT AND/OR PREVENTION OF DIABETES MELLITUS

FIELD OF INVENTION

The present invention relates to the use of a composition comprising glucoraphanin for reducing fasting serum glucose levels in a subject and/or preventing diabetes mellitus and/or a condition associated therewith and/or treating diabetes mellitus and/or a condition associated therewith.

BACKGROUND

Diabetes mellitus, and in particular diabetes mellitus Type II, is a common metabolic disorder that is rapidly increasing particularly in the developed world. The term diabetes mellitus is typically used to refer to a group of metabolic diseases characterised by high blood sugar levels over a prolonged period. There are three main types of diabetes: Type I diabetes mellitus, Type II diabetes mellitus and gestational diabetes mellitus.

Type II diabetes mellitus (non-insulin dependent diabetes) can be characterised by insulin resistance, insulin deficiency and hyperglycaemia.

Type II diabetes may not be diagnosed for many years since symptoms may be sporadic and are certainly milder than those associated with Type I diabetes. However, elevated blood sugar levels in untreated Type II diabetes sufferers can lead to functional impairment of other tissues such as the kidneys and eyes.

SUMMARY OF THE INVENTION

According to a first aspect the present invention provides a composition comprising glucoraphanin for use in:
  a. reducing fasting serum glucose levels in a subject administered with said composition when compared to a subject not administered said composition; and/or
  b. preventing diabetes mellitus and/or a condition associated therewith, treating diabetes mellitus and/or a condition associated therewith, or a combination thereof in a subject;
wherein the composition is intermittently administered to the subject between about 1 to about 5 times per week such that said subject is administered with a weekly dose of between about 300 to about 2500 µmoles of glucoraphanin.

In a second aspect the invention provides a composition prepared from a high glucosinolate cruciferous vegetable, portion thereof, extract thereof or combinations thereof, for use in:
  a. reducing fasting serum glucose levels in a subject administered with said composition when compared to a subject not administered said composition; and/or
  b. preventing diabetes mellitus and/or a condition associated therewith, treating diabetes mellitus and/or a condition associated therewith, or a combination thereof in a subject;
wherein the subject is intermittently administered said composition between about 1 to about 5 times per week such that said subject is administered with a weekly dose of between about 300 to about 2500 µmoles of glucoraphanin.

According to a third aspect there is provided a method of: reducing fasting serum glucose levels in a subject having elevated fasting serum glucose levels; preventing diabetes mellitus and/or a condition associated therewith in a subject; treating a subject having diabetes mellitus and/or a condition associated therewith; or combinations thereof, comprising intermittently administering to a subject a composition comprising:
  a. glucoraphanin; and/or
  b. a composition prepared from a high glucosinolate cruciferous vegetable, portion thereof or extract thereof;
wherein said composition is intermittently administered to the subject between about 1 to about 5 times per week such that said subject is administered with a weekly dose of between about 300 to about 2500 µmoles of glucoraphanin.

In a fourth aspect there is provided the use of a composition comprising glucoraphanin for the manufacture of a medicament for:
  a. reducing fasting serum glucose levels in a subject administered with said composition when compared to a subject not administered said composition; and/or
  b. preventing diabetes mellitus and/or a condition associated therewith, treating diabetes mellitus and/or a condition associated therewith, or a combination thereof in a subject;
wherein the composition is intermittently administered to the subject between about 1 to about 5 times per week such that said subject is administered with a weekly dose of between about 300 to about 2500 µmoles of glucoraphanin.

In a fifth aspect there is provided a use of a composition prepared from a high glucosinolate cruciferous vegetable, portion thereof, extract thereof or combinations thereof, for the manufacture of a medicament for:
  a. reducing fasting serum glucose levels in a subject administered with said composition when compared to a subject not administered said composition; and/or
  b. preventing diabetes mellitus and/or a condition associated therewith, treating diabetes mellitus and/or a condition associated therewith, or a combination thereof in a subject;
wherein the subject is intermittently administered said composition between about 1 to about 5 times per week such that said subject is administered with a weekly dose of between about 300 to about 2500 µmoles of glucoraphanin.

BRIEF DESCRIPTION OF THE DRAWINGS

Embodiments of the invention will now be described, by way of example only, with reference to accompanying drawings, in which:

FIG. 1 shows a sequence alignment between a consensus sequence of the Myb28 locus for broccoli, e.g. *B. villosa*, with an increased level of glucosinolate (FT69) and a consensus sequence of the Myb28 locus for broccoli, e.g. *B. oleracea*, which does not have an increased level of glucosinolate (*Oleracea*). A total of 26 single feature polymorphisms (SFPs) (of which there are 16 SNPs and 10 indels) are detected in a sequence with a total length of 2202 bp. The SFPs are shaded in the sequence alignment shown in FIG. 1. These SFPs are indicative of *B. villosa* introgression.

FIG. 2 shows SEQ ID NO: 1; a sequence of a nucleic acid fragment comprising the Myb28 locus from *Brassica oleracea* (broccoli) which does not have increased glucosinolate levels. The SFPs (including SNPs and indels, e.g. nucleotides that can be deleted) are shaded. The nucleotides between which an SFP (indel insertion) may be inserted are underlined.

FIG. 3 shows SEQ ID NO: 2; a sequence of a nucleic acid fragment comprising the Myb28 locus from *Brassica villosa* FT69 (broccoli) which has increased glucosinolate levels.

The shaded nucleotides indicate SFPs (including SNPs and indels) when aligned with SEQ ID NO: 1.

FIG. 4 shows glucoraphanin content in standard, Beneforte® and Beneforte extra broccoli expressed as micromoles/g fresh weight.

FIG. 5 shows broccoli and stilton soups provided by Bakkavor and packed in a carton designed to freeze soups in individual portions.

FIG. 6 shows level of glucoraphanin (μmoles/g fresh weight) and total sulphur compounds (mg/100 g dry weight) in soups made with standard, Beneforte® and Beneforte extra broccoli. Data obtained from broccoli and stilton soups produced by Bakkavor. Data are expressed as mean±standard deviation, statistical significance is determined using the paired T-test.

FIG. 7 shows fasting blood glucose levels of a subject over a period of 6 years including his 6-months after starting the consumption of Beneforte extra broccoli soups.

FIG. 8 shows fasting blood glucose levels of a cohort of subjects consuming Beneforte extra broccoli soups for 6 months. Data are expressed as mean±standard deviation.

FIG. 9 shows Fold change in fasting blood glucose levels from baseline in a cohort of subjects consuming Beneforte extra broccoli soups, statistical significance is determined using the paired T-test.

FIG. 10 shows change in fasted blood glucose levels compared to baseline in a cohort of subjects consuming Beneforte extra soup.

FIG. 11 shows fasted blood glucose levels compared to baseline in a cohort of subjects consuming a control standard broccoli soup.

DETAILED DESCRIPTION

For the first time the present inventors have shown that a composition comprising glucoraphanin when intermittently administered to a subject between about 1 to about 5 times per week such that said subject is administered with a weekly dose of between about 300 to about 2500 μmoles of glucoraphanin is useful in reducing fasting serum glucose levels in a subject administered with said composition when compared to a subject not administered said composition; and/or preventing diabetes mellitus and/or a condition associated therewith, treating diabetes mellitus and/or a condition associated therewith, or a combination thereof in a subject.

The present inventors have also surprisingly found that a composition prepared from a high glucosinolate cruciferous vegetable, portion thereof, extract thereof or combinations thereof, when intermittently administered to a subject between about 1 to about 5 times per week such that said subject is administered with a weekly dose of between about 300 to about 2500 μmoles of glucoraphanin (suitably for example between about 300 to about 500 μmoles of glucoraphanin) is useful for reducing fasting serum glucose levels in a subject administered with said composition when compared to a subject not administered said composition; and/or preventing diabetes mellitus and/or a condition associated therewith, treating diabetes mellitus and/or a condition associated therewith, or a combination thereof in a subject.

Additionally the inventors have also provided a method of: reducing fasting serum glucose levels in a subject having elevated fasting serum glucose levels; preventing diabetes mellitus and/or a condition associated therewith in a subject; treating a subject having diabetes mellitus and/or a condition associated therewith; or combinations thereof, comprising intermittently administering to a subject a composition comprising:

a. glucoraphanin; and/or
b. a composition prepared from a high glucosinolate cruciferous vegetable, portion thereof or extract thereof;

wherein said composition is intermittently administered to the subject between about 1 to about 5 times per week such that said subject is administered with a weekly dose of between about 300 to about 2500 μmoles of glucoraphanin.

Preferably the composition for use in accordance with the present invention comprises glucoraphanin.

In one embodiment the composition may be prepared from a high glucosinolate cruciferous vegetable. Suitably prepared from a high glucosinolate broccoli plant.

In another embodiment the composition may be prepared from a portion of a high glucosinolate cruciferous vegetable. Suitably prepared from a portion of a high glucosinolate broccoli.

In a further embodiment the composition may be prepared from an extract of a high glucosinolate cruciferous vegetable. Suitably prepared from an extract of a high glucosinolate broccoli.

Suitably the composition described herein is for use in preventing and/or treating diabetes mellitus. More preferably Type II diabetes mellitus.

The term "glucoraphanin" as used herein means 4-methylsulphinylbutyl glucosinolate (MSB). The terms "glucoraphanin", "4-methylsulphinylbutyl glucosinolate" and/or "MSB" are used interchangeably herein. The glucoraphanin for use in accordance with the present invention may be obtainable from any suitable source. Glucoraphanin may be obtainable from a cruciferous vegetable. Suitably glucoraphanin may be obtainable from a broccoli.

Without wishing to be bound by theory it is believed that the glucoraphanin for use in accordance with the present invention may be converted into one or more derivatives thereof in the body of a subject. In some embodiments it may be the derivative thereof that achieves the advantageous effects observed with the present invention.

The term "derivative thereof" refers to a compound that is derived from a glucoraphanin. Suitably the derivative may be an isothiocyanate. Isothiocyanates are sulphur-containing phytochemicals with the general formula R-NCS.

Isothiocyanates occur naturally as glucosinolate conjugates in cruciferous vegetables.

Isothiocyanates of particular interest in the present invention may include the following: 4-methylsulphinylbutyl (otherwise known as sulforaphane or SF); 4-methylthiobutyl (otherwise known as erucin); 4-mercaptobutyl (otherwise known as sativin); β-phenylethylisothiocyanate (PE-ITC); iberin (otherwise know as IB), and 3-methylthiopropyl.

In one embodiment the isothiocyanates in accordance with the present invention may be erucin and/or 3-methylthiopropyl.

In a further embodiment the isothiocyanate may be 3-methylthiopropyl.

In another embodiment the isothiocyanate may be sativin.

Preferably the isothiocyanate and/or derivative of glucoraphanin is 4-methylsulphinylbutyl (sulforaphane).

In another embodiment the composition for use in accordance with the present invention may not comprise sulforaphane.

The composition for use in accordance with the present invention may comprise one or more further glucosinolates and/or derivatives thereof in addition to glucoraphanin.

The glucosinolates are a class of organic compounds that contain sulphur, nitrogen and a group derived from glucose. They occur as secondary metabolites of many plants of the order Brassicales (especially in the family Brassicaceae), such as cruciferous vegetables.

Glucosinolates are water-soluble anions and belong to the glucosides. Every glucosinolate contains a central carbon atom which is bonded via a sulphur atom to the glycone group (making a sulfated ketoxime) and via a nitrogen atom to a sulphate group. In addition, the central carbon is bonded to a side group; different glucosinolates have different side groups.

About 120 different glucosinolates are known to occur naturally in plants.

The glucosinolates in accordance with the present invention are preferably aliphatic.

In the present invention it is envisaged that one or more of the following glucosinolates may be of importance: 4-methylsulphinylbutyl glucosinolate, 3-methylsulphinylpropyl glucosinolate, 4-methylthiobutyl glucosinolate and 3-methylthiopropyl glucosinolate.

In one embodiment the glucosinolate may preferably be 4-methylsulphinylbutyl glucosinolate (MSB) and/or 3-methylsulphinylpropyl glucosinolate (MSP).

In one embodiment the composition for use in accordance with the invention reduces fasting serum glucose levels in a subject administered with the composition.

In order to determine if a subject (e.g. a human subject) displays reduced fasting serum glucose levels it is intended that the skilled person would compare the fasting serum glucose levels of a subject who has been administered the composition described herein with a subject who has not been administered the composition. By comparing the difference in fasting serum glucose levels a reduction can be determined.

Determination of fasting serum glucose levels of a subject can be achieved using any method known in the art. Typically fasting serum glucose levels may be measured using a blood sample from a subject. Suitably fasting serum glucose levels may be determined after the subject has fasted, for example the subject may have fasted for at least 8 hours.

By way of example, fasting glucose concentration can be determined using the glucose assay Ref:3L82-20 and 3L82-40 supplied by Abbott CLINICAL CHEMISTRY. Alternatively, a commercial kit supplied from RANDOX, Cat. No. HA3830 is capable of determining total haemoglobin and glycolated haemoglobin (HbA1c) within a sample. This may be used in combination with an RX Daytona analyzer The term "reducing fasting serum glucose levels" may mean decreasing the fasting serum glucose levels in a subject by at least about 0.25 mmol/L of blood when compared to a subject that has not been administered with the composition herein.

In one embodiment the fasting serum glucose levels of a subject administered with the composition of the invention may be decreased by at least about 0.5 mmol/L of blood when compared to a subject that has not been administered with the composition herein.

In another embodiment the fasting serum glucose levels of a subject administered with the composition of the invention may be decreased by at least about 1.0 mmol/L of blood when compared to a subject that has not been administered with the composition for use in the present invention.

Suitably the fasting serum glucose levels of a subject administered with the composition of the invention may be decreased by at least about 1.5 mmol/L of blood when compared to a subject that has not been administered with the composition for use in the present invention.

The time-frame for observing a reduction of fasting serum glucose levels of a subject administered with the composition of the invention may vary.

In one embodiment the subject may present with reduced fasting serum glucose levels when compared to a subject that has not been administered with the composition herein after administration for at least about 2 weeks, suitably after at least about 1 month.

In another embodiment the subject may present with reduced fasting serum glucose levels when compared to a subject that has not been administered with the composition herein after administration for at least about 3 months. Preferably after administration for less than about 6 months.

In a further embodiment the subject may present with reduced fasting serum glucose levels when compared to a subject that has not been administered with the composition herein after administration for at least about 6 months.

In some embodiments the subject may present with reduced fasting serum glucose levels when compared to a subject that has not been administered with the composition herein after administration for at least about 1 year.

In one embodiment the fasting serum glucose levels of a subject administered with the composition of the invention may be decreased by at least about 0.25 mmol/L of blood when compared to a subject that has not been administered with the composition herein after administration for at least about 2 weeks, at least about 1 month, at least about 6 months or at least about 1 year. Preferably after administration for less than about 6 months.

In one embodiment the fasting serum glucose levels of a subject administered with the composition of the invention may be decreased by at least about 0.5 mmol/L of blood when compared to a subject that has not been administered with the composition herein after administration for at least about 2 weeks, at least about 1 month, at least about 6 months or at least about 1 year. Preferably after administration for less than about 6 months.

In one embodiment the fasting serum glucose levels of a subject administered with the composition of the invention may be decreased by at least about 1.0 mmol/L of blood when compared to a subject that has not been administered with the composition herein after administration for at least about 2 weeks, at least about 1 month, at least about 6 months or at least about 1 year. Preferably after administration for less than about 6 months.

In one embodiment the fasting serum glucose levels of a subject administered with the composition of the invention may be decreased by at least about 1.5 mmol/L of blood when compared to a subject that has not been administered with the composition herein after administration for at least about 2 weeks, at least about 1 month, at least about 6 months or at least about 1 year. Preferably after administration for less than about 6 months.

Cruciferous Vegetables

In one embodiment the glucoraphanin for use in the composition of the present invention may be sourced from a plant.

Glucosinolate is present in plants from the order Capparales. This order includes about 18 families, of which the Brassicaceae and the Capparaceae are the two largest.

The composition for use in accordance with the present invention may be prepared from a cruciferous vegetable, a portion thereof or an extract thereof.

Cruciferous vegetables (e.g. cruciferous vegetable crops) from the family Brassicaceae containing glucosinolate include the following cruciferous vegetable crops:

broccoli
rocket (including *Sisymbrium officinales; Eruca sativa* (Salad Rocket), *Diplotaxis erucoides* (Wall Rocket), *Diplotaxis tenuifolia* (Wild Rocket), and *Bunias orientalis* (Turkish Rocket)); and
watercress (including *Rorripa nasturtium aquaticum* and *Nasturtium officinale*).
cauliflower,
kale,
turnip,
collards,
Brussels sprouts,
cabbage, and
radish.

As used herein, the term "cruciferous vegetable" means a fresh cruciferous vegetable and/or a processed cruciferous vegetable and/or an extract of a cruciferous vegetable.

In one embodiment the term "cruciferous vegetable" as used herein means a fresh cruciferous vegetable.

In a further embodiment the term "cruciferous vegetable" as used herein means a processed cruciferous vegetable.

In another embodiment the term "cruciferous vegetable" as used herein means an extract of a cruciferous vegetable.

The term "fresh cruciferous vegetable" as used herein means a cruciferous vegetable or part thereof either consumed raw or cooked by any suitable method.

The term "processed cruciferous vegetable" as used herein means a cruciferous vegetable which has undergone at least one further processing step such as, for example, floreting, individual quick freezing (IQF), maceration, homogenisation, drying, freezing, compacting etc.

An "extract" of a cruciferous vegetable as used herein refers to a substance or mixture of substances obtained by extracting the whole or part of a fresh cruciferous vegetable as defined herein and/or by extracting the whole or part of a processed cruciferous vegetable as defined herein. The extraction may be carried out using chemical or mechanical action, e.g. by a solvent such as ethanol or water, or by pressure, distillation or evaporation. In one embodiment preferably the extract is an aqueous extract.

In some embodiments the cruciferous vegetable, portion thereof or extract thereof may be a broccoli plant, portion thereof or extract thereof.

In one embodiment suitably the extract comprises at least the glucosinolates or the sulphur compound containing extract of the cruciferous vegetable or broccoli.

In one embodiment, the extract may be a crude extract. Methods for obtaining crude extracts are known in the art. Published methods include, for example, Iris Lee and Mary C. Boyce (Extraction and purification of Glucoraphanin by preparative High-performance Liquid Chromatography (HPLC), J. Chem. Edu., 2011), as well as Mark A. Berhow et al. (Purification of a sinapine-Glucoraphanin Salt from broccoli seeds, American Journal of Plant sciences, 2010).

The term "a portion thereof" in reference to a cruciferous vegetable relates to any part of a cruciferous vegetable including a part of a cruciferous vegetable that has been isolated from another part of the cruciferous vegetable. A "portion thereof" may include florets, inflorescences and/or stems. Suitably the term "portion thereof" may refer to florets of a high glucosinolate cruciferous vegetable.

In one embodiment the composition for use in accordance with the invention may be prepared from a cruciferous vegetable, portion thereof or extract thereof comprising a sulphur concentration of at least about 5.00 mg of sulphur per gram of dry weight, suitably at least about 5.25 mg of sulphur per gram of dry weight.

Preferably at least about 5.40 mg of sulphur per gram of dry weight.

In some embodiments the composition for use in accordance with the invention may be prepared from a cruciferous vegetable, portion thereof or extract thereof comprising a sulphur concentration of between about 5.00 mg of sulphur per gram of dry weight to about 7.00 mg of sulphur per gram of dry weight. Suitably comprising a sulphur concentration between about 5.25 to about 6.00 mg of sulphur per gram of dry weight.

Preferably comprising a sulphur concentration between about 5.40 mg of sulphur per gram of dry weight to about 5.80 mg of sulphur per gram of dry weight.

In one embodiment the composition for use in accordance with the invention may be prepared from a broccoli plant, portion thereof or extract thereof comprising a sulphur concentration of at least about 5.00 mg of sulphur per gram of dry weight, suitably at least about 5.25 mg of sulphur per gram of dry weight.

Preferably at least about 5.40 mg of sulphur per gram of dry weight.

In some embodiments the composition for use in accordance with the invention may be prepared from a broccoli plant, portion thereof or extract thereof comprising a sulphur concentration of between about 5.00 mg of sulphur per gram of dry weight to about 7.00 mg of sulphur per gram of dry weight. Suitably comprising a sulphur concentration between about 5.25 to about 6.00 mg of sulphur per gram of dry weight.

Preferably comprising a sulphur concentration between about 5.40 mg of sulphur per gram of dry weight to about 5.80 mg of sulphur per gram of dry weight.

In one embodiment the composition for use in accordance with the invention may be prepared form a high glucosinolate cruciferous vegetable.

The term "high glucosinolate cruciferous vegetable" as used herein means a cruciferous vegetable comprising at least about 20 µmoles/g fresh weight of glucoraphanin.

In one embodiment a high glucosinolate cruciferous vegetable may comprise at least about 30 µmoles/g fresh weight of glucoraphanin. Preferably a high glucosinolate vegetable may comprise at least about 32 µmoles/g fresh weight of glucoraphanin.

Suitably a high glucosinolate cruciferous vegetable may comprise about 32 µmoles/g fresh weight of glucoraphanin.

In another embodiment a high glucosinolate cruciferous vegetable may comprise between about 20 to about 50 µmoles/g fresh weight of glucoraphanin. Suitably between about 25 to about 45 µmoles/g fresh weight of glucoraphanin. Suitably between about 27 to about 45 µmoles/g fresh weight of glucoraphanin. More suitably between about 27 to about 40 µmoles/g fresh weight of glucoraphanin.

In another embodiment a high glucosinolate cruciferous vegetable may comprise between about 27 to about 38 µmoles/g fresh weight of glucoraphanin. Suitably between about 27 to about 35 µmoles/g fresh weight of glucoraphanin. More suitably between about 30 to about 35 µmoles/g fresh weight of glucoraphanin.

In one embodiment the high glucosinolate cruciferous vegetable (preferably a *Brassica*) may be a cruciferous vegetable (preferably a *Brassica*) having Myb28-mediated increased glucosinolate levels.

In one embodiment the cruciferous vegetable (preferably a *Brassica*) having Myb28-mediated increased glucosinolate levels may comprise a polymorphic Myb28 locus from *Brassica villosa*. Preferably the cruciferous vegetable (preferably a *Brassica*) having Myb28-mediated increased glucosinolate levels may be homozygous for the polymorphic Myb28 locus from *Brassica villosa*.

In one embodiment, a polymorphic Myb28 locus (also referred to herein as "FT69" and/or a "FT69 (increased glucosinolate)" sequence) is represented as the FT69 sequence shown in FIG. 1.

In another embodiment, a Myb28 FT69 (increased glucosinolate) sequence is represented as the FT69 sequence shown as SEQ ID NO: 2 (in FIG. 3).

In one embodiment the high glucosinolate cruciferous vegetable (preferably a *Brassica*) may be a high glucosinolate cruciferous vegetable (preferably a *Brassica*) comprising SEQ ID No. 1 except for at least one polymorphism selected from the group consisting of:
 a) a single nucleotide polymorphism (SNP) at a position corresponding to nucleotide 83, 136, 226, 563, 610, 830, 995, 1116, 1513, 1577, 1606, 1620, 1825, 1863, 1877 or 2026 of SEQ ID NO: 1, or
 b) a polymorphism in the number of nucleotides present between nucleotides 323 and 332, between nucleotides 521 and 524, between nucleotides 783 and 786, between nucleotides and 909 and 914, between nucleotides 1365 and 1369, between 1811 and 1821, or between nucleotides 2046 and 2056 of SEQ ID NO: 1, or
 c) a polymorphism in the number of nucleotides present between nucleotides 836 and 837, between nucleotides 867 and 868, or between nucleotides 943 and 944 of SEQ ID NO: 1.

Preferably the high glucosinolate cruciferous vegetable (preferably a *Brassica*) may be a high glucosinolate cruciferous vegetable (preferably a *Brassica*) comprising at least 2 copies SEQ ID No. 1 except for at least one polymorphism selected from the group consisting of:
 a) a single nucleotide polymorphism (SNP) at a position corresponding to nucleotide 83, 136, 226, 563, 610, 830, 995, 1116, 1513, 1577, 1606, 1620, 1825, 1863, 1877 or 2026 of SEQ ID NO: 1, or
 b) a polymorphism in the number of nucleotides present between nucleotides 323 and 332, between nucleotides 521 and 524, between nucleotides 783 and 786, between nucleotides and 909 and 914, between nucleotides 1365 and 1369, between 1811 and 1821, or between nucleotides 2046 and 2056 of SEQ ID NO: 1, or
a polymorphism in the number of nucleotides present between nucleotides 836 and 837, between nucleotides 867 and 868, or between nucleotides 943 and 944 of SEQ ID NO: 1.

In other words the high glucosinolate cruciferous vegetable (preferably a *Brassica*) may be a high glucosinolate cruciferous vegetable (preferably a *Brassica*) which is homozygous for SEQ ID No. 1 having one or more of the polymorphisms selected from the group consisting of:
 a) a single nucleotide polymorphism (SNP) at a position corresponding to nucleotide 83, 136, 226, 563, 610, 830, 995, 1116, 1513, 1577, 1606, 1620, 1825, 1863, 1877 or 2026 of SEQ ID NO: 1, or
 b) a polymorphism in the number of nucleotides present between nucleotides 323 and 332, between nucleotides 521 and 524, between nucleotides 783 and 786, between nucleotides and 909 and 914, between nucleotides 1365 and 1369, between 1811 and 1821, or between nucleotides 2046 and 2056 of SEQ ID NO: 1, or
a polymorphism in the number of nucleotides present between nucleotides 836 and 837, between nucleotides 867 and 868, or between nucleotides 943 and 944 of SEQ ID NO: 1.

In one embodiment the high glucosinolate cruciferous vegetable (preferably a *Brassica*) may be a high glucosinolate cruciferous vegetable (preferably a *Brassica*) comprising SEQ ID NO: 2 or a sequence which has a least 97% (such as at least 98% or at least 99%) identity with SEQ ID NO: 2. Suitably, comprising at least 2 copies (e.g. being homozygous) of SEQ ID NO: 2 or a sequence which has a least 97% (such as at least 98% or at least 99%) identity with SEQ ID NO: 2.

Suitably the high glucosinolate cruciferous vegetable (preferably a *Brassica*) may be a high glucosinolate cruciferous vegetable (preferably a *Brassica*) comprising SEQ ID NO: 2. Preferably comprising at least 2 copies (e.g. being homozygous) of SEQ ID NO: 2.

Suitably the high glucosinolate cruciferous vegetable having Myb28-mediated increased glucosinolate levels may be one taught in EP2708607A2 and/or EP2708115A1 (the contents of which are incorporated herein in their entirety) and/or identified by one or more of the methods taught therein.

In one embodiment the high glucosinolate cruciferous vegetable (preferably a *Brassica*) may comprise a Myb28 allele (preferably a least 2 Myb28 alleles) from *Brassica villosa* and lack an ELONG allele from *Brassica villosa* genetically linked to the Myb28 allele. Such a high glucosinolate cruciferous vegetable may be one as taught in EP2708115A1.

High Glucosinolate Broccoli

In some embodiments the composition and/or composition comprising glucoraphanin for use in the present invention may be prepared from a high glucosinolate broccoli plant, portion thereof, extract thereof or combinations thereof.

The terms "broccoli" and "broccoli plant" are used synonymously herein.

As used herein, the term "broccoli" means fresh broccoli and/or processed broccoli and/or an extract of broccoli.

In one embodiment the term "broccoli" as used herein means fresh broccoli.

In a further embodiment the term "broccoli" as used herein means processed broccoli.

In another embodiment the term "broccoli" as used herein means an extract of broccoli.

The term "fresh broccoli" as used herein means broccoli inflorescences and stems either consumed raw or cooked by any suitable method.

The term "processed broccoli" as used herein means broccoli which has undergone at least one further processing step such as, for example, floreting, individual quick freezing (IQF), maceration, homogenisation, drying, freezing, compacting etc.

"An extract of broccoli" or "broccoli extract" as used herein refers to a substance or mixture of substances obtained by extracting the whole or part of fresh broccoli as defined herein and/or by extracting the whole or part of processed broccoli as defined herein. The extraction may be carried out using a solvent such as ethanol or water. In one embodiment preferably the extract is an aqueous extract. In one embodiment suitably the extract comprises at least the glucosinolates of the broccoli.

The term "portion thereof" as used herein in reference to a broccoli (e.g. a high glucosinolate broccoli) refers to any part of a broccoli plant. In some embodiments the term "portion thereof" may refer to broccoli florets, inflorescences and/or stems.

Suitably the term "portion thereof" may refer to broccoli florets.

Suitably the term "portion thereof" may refer to broccoli inflorescences. Preferably broccoli inflorescences of a high glucosinolate broccoli.

The term "high glucosinolate broccoli" as used herein means a broccoli comprising at least about 20 µmoles/g fresh weight of glucoraphanin. In one embodiment the term "high glucosinolate broccoli" as used herein means a broccoli comprising at least about 25 µmoles/g fresh weight of glucoraphanin.

In one embodiment a high glucosinolate broccoli may comprise at least about 30 µmoles/g fresh weight of glucoraphanin. Preferably a high glucosinolate vegetable may comprise at least about 32 µmoles/g fresh weight of glucoraphanin.

Suitably a high glucosinolate broccoli may comprise about 32 µmoles/g fresh weight of glucoraphanin.

In another embodiment a high glucosinolate broccoli may comprise between about 20 to about 50 µmoles/g fresh weight of glucoraphanin. Suitably between about 25 to about 45 µmoles/g fresh weight of glucoraphanin. Suitably between about 27 to about 45 µmoles/g fresh weight of glucoraphanin. More suitably between about 27 to about 40 µmoles/g fresh weight of glucoraphanin.

In another embodiment a high glucosinolate broccoli may comprise between about 27 to about 38 µmoles/g fresh weight of glucoraphanin. Suitably between about 27 to about 35 µmoles/g fresh weight of glucoraphanin. More suitably between about 30 to about 35 µmoles/g fresh weight of glucoraphanin.

In one embodiment the high glucosinolate broccoli may have Myb28-mediated increased glucosinolate levels.

In one embodiment the high glucosinolate broccoli having Myb28-mediated increased glucosinolate levels may comprise a polymorphic Myb28 locus from *Brassica villosa*. Preferably the high glucosinolate broccoli having Myb28-mediated increased glucosinolate levels may be homozygous for the polymorphic Myb28 locus from *Brassica villosa*.

In another embodiment the high glucosinolate broccoli may be a high glucosinolate broccoli comprising SEQ ID No. 1 except for at least one polymorphism selected from the group consisting of:
a) a single nucleotide polymorphism (SNP) at a position corresponding to nucleotide 83, 136, 226, 563, 610, 830, 995, 1116, 1513, 1577, 1606, 1620, 1825, 1863, 1877 or 2026 of SEQ ID NO: 1, or
b) a polymorphism in the number of nucleotides present between nucleotides 323 and 332, between nucleotides 521 and 524, between nucleotides 783 and 786, between nucleotides and 909 and 914, between nucleotides 1365 and 1369, between 1811 and 1821, or between nucleotides 2046 and 2056 of SEQ ID NO: 1, or
c) a polymorphism in the number of nucleotides present between nucleotides 836 and 837, between nucleotides 867 and 868, or between nucleotides 943 and 944 of SEQ ID NO: 1.

Preferably the high glucosinolate broccoli may be a high glucosinolate broccoli comprising at least 2 copies SEQ ID No. 1 except for at least one polymorphism selected from the group consisting of:
a) a single nucleotide polymorphism (SNP) at a position corresponding to nucleotide 83, 136, 226, 563, 610, 830, 995, 1116, 1513, 1577, 1606, 1620, 1825, 1863, 1877 or 2026 of SEQ ID NO: 1, or
b) a polymorphism in the number of nucleotides present between nucleotides 323 and 332, between nucleotides 521 and 524, between nucleotides 783 and 786, between nucleotides and 909 and 914, between nucleotides 1365 and 1369, between 1811 and 1821, or between nucleotides 2046 and 2056 of SEQ ID NO: 1, or a polymorphism in the number of nucleotides present between nucleotides 836 and 837, between nucleotides 867 and 868, or between nucleotides 943 and 944 of SEQ ID NO: 1.

In other words the high glucosinolate broccoli may be a high glucosinolate broccoli which is homozygous for SEQ ID No. 1 having one or more of the polymorphisms selected from the group consisting of:
a) a single nucleotide polymorphism (SNP) at a position corresponding to nucleotide 83, 136, 226, 563, 610, 830, 995, 1116, 1513, 1577, 1606, 1620, 1825, 1863, 1877 or 2026 of SEQ ID NO: 1, or
b) a polymorphism in the number of nucleotides present between nucleotides 323 and 332, between nucleotides 521 and 524, between nucleotides 783 and 786, between nucleotides and 909 and 914, between nucleotides 1365 and 1369, between 1811 and 1821, or between nucleotides 2046 and 2056 of SEQ ID NO: 1, or a polymorphism in the number of nucleotides present between nucleotides 836 and 837, between nucleotides 867 and 868, or between nucleotides 943 and 944 of SEQ ID NO: 1.

In one embodiment the high glucosinolate broccoli may be a high glucosinolate broccoli comprising SEQ ID NO: 2 or a sequence which has a least 97% (such as at least 98% or at least 99%) identity with SEQ ID NO: 2. Suitably, comprising at least 2 copies (e.g. being homozygous) of SEQ ID NO: 2 or a sequence which has a least 97% (such as at least 98% or at least 99%) identity with SEQ ID NO: 2.

Suitably the high glucosinolate broccoli may be a high glucosinolate broccoli comprising SEQ ID NO: 2. Preferably comprising at least 2 copies (e.g. being homozygous) of SEQ ID NO: 2.

Suitably the high glucosinolate broccoli having Myb28-mediated increased glucosinolate levels may be one taught in EP2708607A2 and/or identified by one or more of the methods taught therein.

In one embodiment the high glucosinolate broccoli may comprise a Myb28 allele (preferably a least 2 Myb28 alleles) from *Brassica villosa* and lack an ELONG allele from *Brassica villosa* genetically linked to the Myb28 allele. Such a high glucosinolate broccoli may be one as taught in EP2708115A1.

Preferably the broccoli is a *Brassica oleracea* plant.

The term "Myb28$^{Villosa}$" is used herein to refer to a Myb28 gene obtainable from *Brassica villosa*.

Administration

The composition for use in accordance with the present invention may be "intermittently administered".

The term "intermittently administered" as used herein means that for at least 1 day, suitably at least 2, 3, 4, 5 or 6 days in a week the subject is not administered the composition for use in the present invention. Preferably the term "intermittent" as used herein means that for 6 days in a week the subject is not administered the composition for use in the present invention.

Therefore preferably a subject is not administered with a composition for use in accordance with the invention daily for a week or more.

Without wishing to be bound by theory the inventors believe that significantly better results can be achieved by intermittent administration when compared to continuous administration. It is believed that providing a "pulse" of glucoraphanin is more beneficial for reducing fasting serum glucose levels in a subject and/or preventing diabetes mellitus and/or a condition associated therewith and/or treating diabetes mellitus and/or a condition associated therewith. It is further believed that by continually administering a subject with glucoraphanin or a derivative of glucoraphanin (such as sulforaphane) that the metabolism and/or physiology of the subject adapts to the continuous presence of glucoraphanin and/or derivative thereof and that this results in a reduction in the effectiveness of the composition for use in the invention.

The inventors have found that intermittent administration as per the invention results in a "pulse" of glucoraphanin, which triggers metabolic changes in a subject administered with the composition. Advantageously, it is believed that due to intermittent administration and the "pulse" effect observed that only a low dose of glucoraphanin needs to be administered to a subject to reduce fasting serum glucose levels in a subject and/or prevent diabetes mellitus and/or a condition associated therewith and/or treat diabetes mellitus and/or a condition associated therewith.

Lower dosages of glucoraphanin will also reduce the risk of any side-effects associated with the administration thereof.

The composition for use in accordance with the invention is intermittently administered such that a subject is administered with a weekly dose of between about 300 to about 2500 µmoles of glucoraphanin.

The composition for use in accordance with the invention is intermittently administered such that a subject is administered with a weekly dose of between about 300 to about 2000 µmoles of glucoraphanin.

Suitably the composition for use in accordance with the invention is intermittently administered such that a subject is administered with a weekly dose of between about 300 to about 1400 µmoles of glucoraphanin.

Suitably the composition for use in accordance with the invention is intermittently administered such that a subject is administered with a weekly dose of between about 300 to about 950 µmoles of glucoraphanin.

Suitably the composition for use in accordance with the invention is intermittently administered such that a subject is administered with a weekly dose of between about 300 to about 500 µmoles of glucoraphanin.

Suitably the composition for use in accordance with the invention is intermittently administered such that a subject is administered with a weekly dose of between about 350 to about 480 µmoles of glucoraphanin.

In one embodiment the composition for use in the present invention may be intermittently administered to a subject between about 1 to about 5 times per week such that a subject is administered with a weekly dose of between about 300 to about 2500 µmoles of glucoraphanin.

In one embodiment the composition for use in the present invention may be intermittently administered to a subject between about 1 to about 5 times per week such that a subject is administered with a weekly dose of between about 300 to about 2000 µmoles of glucoraphanin.

In one embodiment the composition for use in the present invention may be intermittently administered to a subject between about 1 to about 5 times per week such that a subject is administered with a weekly dose of between about 300 to about 1400 µmoles of glucoraphanin.

In one embodiment the composition for use in the present invention may be intermittently administered to a subject between about 1 to about 5 times per week such that a subject is administered with a weekly dose of between about 300 to about 950 µmoles of glucoraphanin.

In one embodiment the composition for use in the present invention may be intermittently administered to a subject between about 1 to about 5 times per week such that a subject is administered with a weekly dose of between about 300 to about 500 µmoles of glucoraphanin.

Suitably the composition for use in the present invention may be intermittently administered to a subject between about 1 to about 5 times per week such that a subject is administered with a weekly dose of between about 350 to about 480 µmoles of glucoraphanin.

In a further embodiment the composition for use in the present invention may be intermittently administered to a subject between about 1 to about 3 times per week (suitably 2 times per week) such that a subject is administered with a weekly dose of between about 300 to about 2500 µmoles of glucoraphanin.

In a further embodiment the composition for use in the present invention may be intermittently administered to a subject between about 1 to about 3 times per week (suitably 2 times per week) such that a subject is administered with a weekly dose of between about 300 to about 2000 µmoles of glucoraphanin.

In a further embodiment the composition for use in the present invention may be intermittently administered to a subject between about 1 to about 3 times per week (suitably 2 times per week) such that a subject is administered with a weekly dose of between about 300 to about 1400 µmoles of glucoraphanin.

In a further embodiment the composition for use in the present invention may be intermittently administered to a subject between about 1 to about 3 times per week (suitably 2 times per week) such that a subject is administered with a weekly dose of between about 300 to about 950 µmoles of glucoraphanin.

In a further embodiment the composition for use in the present invention may be intermittently administered to a subject between about 1 to about 3 times per week (suitably 2 times per week) such that a subject is administered with a weekly dose of between about 300 to about 500 µmoles of glucoraphanin.

Suitably the composition for use in the present invention may be intermittently administered to a subject between about 1 to about 3 times per week (suitably 2 times per week) such that a subject is administered with a weekly dose of between about 350 to about 480 µmoles of glucoraphanin.

In a further embodiment the composition for use in the present invention may be intermittently administered to a subject once per week such that a subject is administered with a weekly dose of between about 300 to about 2500 µmoles of glucoraphanin.

In a further embodiment the composition for use in the present invention may be intermittently administered to a subject once per week such that a subject is administered with a weekly dose of between about 300 to about 2000 µmoles of glucoraphanin.

In a further embodiment the composition for use in the present invention may be intermittently administered to a subject once per week such that a subject is administered with a weekly dose of between about 300 to about 1400 µmoles of glucoraphanin.

In a further embodiment the composition for use in the present invention may be intermittently administered to a subject once per week such that a subject is administered with a weekly dose of between about 300 to about 950 µmoles of glucoraphanin.

Suitably the composition for use in the present invention may be intermittently administered to a subject once per week such that a subject is administered with a weekly dose of between about 300 to about 500 µmoles of glucoraphanin.

Suitably the composition for use in the present invention may be intermittently administered to a subject once per week such that a subject is administered with a weekly dose of between about 350 to about 480 µmoles of glucoraphanin.

In a particularly preferred embodiment a subject may be administered with a composition for use in the present invention once per week.

In some embodiments the composition for use in the present invention may have a concentration of between about 0.2 µmoles/ml to about 1.7 µmoles/ml of glucoraphanin. Suitably, between about 0.5 µmoles/ml to about 1.5 µmoles/ml of glucoraphanin. Preferably between about 0.75 µmoles/ml to about 1.5 µmoles/ml of glucoraphanin.

The term "administered" includes delivery by any techniques known to a person skilled in the art.

The composition for use in accordance with the present invention may be administered alone but may be administered as a pharmaceutical composition—e.g. when the composition is in admixture with a suitable pharmaceutical excipient, diluent or carrier selected with regard to the intended route of administration and standard pharmaceutical practice.

For example, the composition can be administered (e.g. orally, such as in the form of a foodstuff (e.g. a soup) or topically) in the form of tablets, capsules, ovules, elixirs, solutions or suspensions, which may contain flavouring or colouring agents, for immediate-, delayed-, modified-, sustained-, pulsed- or controlled-release applications.

Preferably the composition may be orally administered.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

The routes for administration (delivery) include, but are not limited to, one or more of: oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, subcutaneous, transdermal, rectal, buccal, sublingual.

If the composition of the present invention is administered parenterally, then examples of such administration include one or more of: intravenously, intra-arterially, intraperitoneally, intrathecally, intraventricularly, intraurethrally, intrasternally, intracranially, intramuscularly or subcutaneously administering the agent; and/or by using infusion techniques.

For parenteral administration, the composition is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

As indicated, the composition of the present invention can be administered intranasally or by inhalation and is conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A™) or 1,1,1,2,3,3,3-heptafluoropropane (HFA 227EA™), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of the agent and a suitable powder base such as lactose or starch.

Alternatively, the composition of the present invention can be administered in the form of a suppository or pessary, or it may be applied topically in the form of a gel, hydrogel, lotion, solution, cream, ointment or dusting powder. The agent of the present invention may also be dermally or transdermally administered, for example, by the use of a skin patch. They may also be administered by the pulmonary or rectal routes. They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the composition of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compositions of the present invention may be administered by direct injection.

In a particularly preferred embodiment the composition for use in the present invention may be administered orally.

In some embodiments when the composition may be administered orally it is administered in the form of an edible portion of a high glucosinolate vegetable crop (e.g. a high glucosinolate broccoli).

In a particularly preferred embodiment the composition for use in the present invention may be administered as a foodstuff. Suitably a liquid foodstuff (e.g. a soup).

In some embodiments the foodstuff may be a food product, preferably a prepared food product. Suitably the prepared food product may be a soup.

Forms And Formulations

The composition for use in accordance with the present invention may be formulated in any suitable manner known to one skilled in the art. The composition may comprise glucoraphanin from any known source. The glucoraphanin may be of a natural or synthetic origin. In one embodiment the glucoraphanin may be substantially isolated and/or purified.

In some embodiments the composition for use in the present invention may be supplemented with natural and/or synthetic glucoraphanin. Suitably the glucoraphanin with which the composition may be supplemented may be in a substantially isolated and/or purified form.

In other embodiments the composition for use in accordance with the present invention may comprise or consist of glucoraphanin in a substantially isolated and/or purified form.

The term "substantially isolated" as used herein means that a compound (e.g. glucoraphanin) is free from other compounds with which it may be present, such as contaminants (e.g. contaminants that might be found in nature). The term "substantially isolated" may mean that a composition comprises at least about 90% concentration w/w of a compound of interest (e.g. glucoraphanin). Suitably a composition may comprise at least about 95% concentration w/w of a compound of interest, more suitably at least 99% concentration w/w of a compound of interest.

The term "substantially purified" as used herein means that a compound (e.g. glucoraphanin) has undergone a process to isolate it from other compounds with which it may be present, such as contaminants (e.g. contaminants that might be found in nature). The term "substantially purified" may mean that a composition comprises at least about 90% concentration w/w of a compound of interest (e.g. glucoraphanin). Suitably a composition may comprise at least about 95% concentration w/w of a compound of interest, more suitably at least 99% concentration w/w of a compound of interest.

In one embodiment, the composition for use in accordance with the present invention may be a crude extract, e.g. a crude extract of a cruciferous vegetable, e.g a high glucosinolate broccoli. Methods for obtaining crude extracts are known in the art. Published methods include, for example, Iris Lee and Mary C. Boyce (Extraction and purification of Glucoraphanin by preparative High-performance Liquid Chromatography (HPLC), J. Chem. Edu., 2011), as well as Mark A. Berhow et al. (Purification of a sinapine-Glucoraphanin Salt from broccoli seeds, American Journal of Plant sciences, 2010).

In one embodiment the composition for use in accordance with the present invention may be formulated as a foodstuff, a vegetable extract and/or a pharmaceutical composition.

Such a formulation may take any form known in the art, for example the composition formulated in accordance with the foregoing embodiment may be in a solid or liquid form. In some embodiments the composition may be formulated as a powder and/or a tablet.

In a preferred embodiment the composition for use in accordance with the present invention may be formulated as an extract (e.g. a vegetable extract).

The composition of the present invention may be used as—or in the preparation of—a food. Here, the term "food" is used in a broad sense—and covers food for humans as well as food for animals (i.e. a feed). In a preferred aspect, the food is for human consumption.

The food may be in the form of a solution or as a solid—depending on the use and/or the mode of application and/or the mode of administration.

When used as—or in the preparation of—a food—such as functional food—the composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient. The composition of the present invention may be used as a food ingredient.

As used herein the term "food ingredient" includes a formulation which is or can be added to functional foods or foodstuffs as a nutritional supplement and/or fiber supplement. The term food ingredient as used here also refers to formulations which can be used at low levels in a wide variety of products that require gelling, texturising, stabilising, suspending, film-forming and structuring, retention of juiciness and improved mouthfeel, without adding viscosity.

The food ingredient may be in the form of a solution or as a solid—depending on the use and/or the mode of application and/or the mode of administration.

The composition of the present invention may be—or may be added to—food supplements.

The composition of the present invention may be—or may be added to—functional foods.

As used herein, the term "functional food" means food which is capable of providing not only a nutritional effect and/or a taste satisfaction, but is also capable of delivering a further beneficial effect to consumer.

Accordingly, functional foods are ordinary foods that have components or ingredients (such as those described herein) incorporated into them that impart to the food a specific functional—e.g. medical or physiological benefit—other than a purely nutritional effect.

Although there is no legal definition of a functional food, most of the parties with an interest in this area agree that they are foods marketed as having specific health effects. Some functional foods are nutraceuticals. Here, the term "nutraceutical" means a food which is capable of providing not only a nutritional effect and/or a taste satisfaction, but is also capable of delivering a therapeutic (or other beneficial) effect to the consumer. Nutraceuticals cross the traditional dividing lines between foods and medicine.

Surveys have suggested that consumers place the most emphasis on functional food claims relating to heart disease. Preventing cancer is another aspect of nutrition which interests consumers a great deal, but interestingly this is the area that consumers feel they can exert least control over. In fact, according to the World Health Organization, at least 35% of cancer cases are diet-related. Furthermore claims relating to osteoporosis, gut health and obesity effects are also key factors that are likely to incite functional food purchase and drive market development.

For certain aspects, the foodstuff may be a beverage.

The present invention also provides a method of preparing a food or a food ingredient, the method comprising admixing a high glucosinolate cruciferous vegetable (preferably a high glucosinolate broccoli) according to the present invention or the composition according to the present invention with another food ingredient. The method for preparing or a food ingredient is also another aspect of the present invention.

In one embodiment the foodstuff may comprise a high glucosinolate cruciferous vegetable (preferably a high glucosinolate broccoli).

Suitably the foodstuff may comprise the florets of a high glucosinolate cruciferous vegetable (preferably a high glucosinolate broccoli).

In a particularly preferred embodiment the foodstuff may be a processed and/or prepared food product.

The processed and/or prepared food product may be any suitably processed and/or prepared food product known in the art.

In one embodiment the processed and/or prepared food product may be one or more selected from the group consisting of: a soup, a juice, a smoothie, a spread, a yogurt, a sauce, a gravy, a tart, a quiche, a pie, a prepared vegetable product (such a vegetable bake) and a blended product (e.g. a blended vegetable product).

In some embodiments the processed and/or prepared food product may be a soup, a gravy and/or a sauce.

Preferably the prepared processed and/or prepared food product may be a soup.

In some embodiments where an extract of a cruciferous vegetable is used to prepare processed and/or prepared food product the food product may be one or more selected from the group consisting of: a juice, a smoothie, a sauce, a spread and a yogurt.

In other embodiments the processed and/or prepared foodstuff of the foregoing embodiments may comprise a high glucosinolate cruciferous vegetable (preferably a high glucosinolate broccoli).

Suitably the processed and/or prepared foodstuff comprising a high glucosinolate cruciferous vegetable (preferably a high glucosinolate broccoli) may be one or more selected from the group consisting of: a soup, a sauce, a gravy, a tart, a quiche, a pie, a prepared vegetable product (such a vegetable bake) and a blended product (e.g. a blended vegetable product).

Preferably the processed and/or prepared foodstuff comprising a high glucosinolate cruciferous vegetable (preferably a high glucosinolate broccoli) may be one or more selected from the group consisting of a soup, a gravy and a sauce.

More preferably the processed and/or prepared foodstuff comprising a high glucosinolate Cruciferous vegetable (preferably a high glucosinolate broccoli) may be a soup.

An exemplary recipe for such a soup is provided below.

In one embodiment the soup may comprise the following ingredients: water, high glucosinolate broccoli (28%), fresh milk, single cream, diced onion potato, stilton cheese (4%), cornflour, rapeseed oil, salt, black pepper.

In one embodiment the composition comprising glucoraphanin may be formulated using an extract of a vegetable enriched in glucosinolate.

In one embodiment the composition for use in the invention may comprise an extract from a high glucosinolate cruciferous vegetable (such as a high glucosinolate broccoli), which extract also has a high level of glucosinolate (preferably glucoraphanin).

In one embodiment the extract may be a substance or mixture of substances obtained by extracting the whole or part of a fresh high glucosinolate cruciferous vegetable (such as a high glucosinolate broccoli) as defined herein (including a raw cruciferous vegetable (such as raw broccoli)) or by extracting the whole or part of a processed cruciferous vegetable (such as processed broccoli) as defined herein.

The extraction may be carried out using a solvent such as ethanol or water. In one embodiment preferably the extract is an aqueous extract.

In one embodiment the composition for use in accordance with the invention may comprise an extract from a *Brassica* plant, suitably a *Brassica oleracea* (e.g. broccoli) plant.

In a particularly preferred embodiment the composition for use in the present invention may be comprise an extract from a Myb28$^{Villosoa}$ homozygous plant.

Preferably the composition may comprise an extract from a Myb28$^{Villosoa}$ homozygous broccoli plant. A suitably Myb28$^{Villosoa}$ homozygous broccoli plant may be one taught in EP2708607A2 which document is incorporated herein by reference.

When the composition of the invention is formulated as a pharmaceutical composition such a composition may comprise a therapeutically effective amount of the agent(s) of the present invention and a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as (or in addition to) the carrier, excipient or diluent any suitable binder(s), lubricant(s), suspending agent(s), coating agent(s), solubilising agent(s).

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be administered using a mini-pump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be administered by a number of routes.

Where the agent is to be administered orally or mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

The composition for use in the present invention (e.g. the foodstuff or food product) may be in any form, e.g. liquid or solid.

Suitably the composition for use in accordance with the present invention may be frozen or lyophilised (freeze-dried).

Suitably the composition for use in accordance with the present invention may be pasteurised (e.g. pasteurised at 70-80° C. for 5-20 seconds).

In one embodiment the composition for use in accordance with the present invention may be a liquid pasteurised composition. In one embodiment the composition for use in accordance with the present invention may be a liquid pasturised foodstuff or food product, such as a liquid or pasteurised soup, sauce, gravy, or blended product (e.g. blended vegetable product).

In one embodiment the composition for use in the present invention may be a frozen composition. In one embodiment the composition for use in accordance with the present invention may be a frozen foodstuff or food product, such as a frozen soup, sauce, gravy, or blended product (e.g. blended vegetable product).

Individual/Subject

As used herein, the terms "individual" and "subject" refers to vertebrates, particularly members of the mammalian species. The term includes but is not limited to domestic animals, sports animals, primates and humans.

In one embodiment preferably the subject is a human.

Diabetes Mellitus

The composition for use in accordance with the present invention is particularly useful for preventing and/or treating diabetes mellitus and/or a condition associated therewith.

The term "condition associated therewith" means an additional disease and/or symptom and/or complication caused by diabetes mellitus. As used herein a "condition associated with diabetes mellitus" means one or more selected from the group consisting of: high blood sugar, frequent urination, increased thirst, diabetic ketoacidosis, nonketotic hyperosmolar coma, foot ulcers, insulin resistance, insulin deficiency and hyperglycaemia.

In one embodiment the composition for use in accordance with the present invention may be used for preventing diabetes mellitus and/or a condition associated therewith.

Suitably the composition for use in accordance with the present invention may be used for preventing diabetes mellitus.

In another embodiment the composition for use in accordance with the present invention may be used for treating diabetes mellitus and/or a condition associated therewith.

Suitably the composition for use in accordance with the present invention may be used for treating diabetes mellitus.

The term "diabetes mellitus" refers to a group of metabolic diseases characterised by high blood sugar levels over a prolonged period. Symptoms of high blood sugar include frequent urination, increased thirst, and increased hunger. If left untreated, diabetes can cause many complications. Acute complications include diabetic ketoacidosis and nonketotic hyperosmolar coma. Serious long-term complications may include inter alia kidney failure, foot ulcers and eye damage.

There are three main types of diabetes mellitus: Type I, Type II and gestational diabetes.

Type I diabetes mellitus typically results from the inability of a subject to produce sufficient amounts of insulin. Type I diabetes mellitus may also be referred to as "insulin dependent diabetes mellitus" or "juvenile diabetes".

Type II diabetes mellitus is typically characterised by the development of insulin resistance by a subject. This form of diabetes may also be referred to as "non insulin-dependent diabetes mellitus" or "adult-onset diabetes". Without wishing to be bound by theory it is believed that a primary cause of Type II diabetes mellitus is a excessive body weight and/or a lack of exercise.

Gestational diabetes mellitus is a form of the disease in which pregnant women with a previous history of diabetes may develop a high blood glucose level.

In one embodiment the composition for use in the present invention may be for use in treating and/or preventing Type II diabetes mellitus and/or a condition associated therewith.

Suitably the composition for use in the present invention may be for use in treating Type II diabetes mellitus and/or a condition associated therewith. Preferably the composition for use in the present invention may be for use in treating Type II diabetes mellitus.

Suitably the composition for use in the present invention may be for use in preventing Type II diabetes mellitus and/or a condition associated therewith. Preferably the composition for use in the present invention may be for use in preventing Type II diabetes mellitus.

Type II diabetes can be characterised by insulin resistance, insulin deficiency and/or hyperglycaemia.

In other embodiments of the invention where the composition is used for preventing diabetes mellitus and/or a condition associated therewith the composition may be administered to a pre-diabetic subject.

The term "pre-diabetic subject" as used herein means a subject presenting with early stages of Type II diabetes. For example, a subject presenting with impaired fasting glycaemia and/or impaired glucose tolerance. Suitably a "pre-diabetic subject" is not a subject that is showing symptoms of sufficient severity for a diagnosis of Type II diabetes to be made.

In some embodiments a "pre-diabetic subject" may be a subject for whom the symptoms that the subject is presenting with can be reversed. In other words a pre-diabetic subject may be a subject that can be restored to a non-disease and/or physiologically normal state.

The WHO diabetes diagnostic criteria are presented in the table below:

| Condition | 2 hour glucose | | Fasting glucose | | HbA$_{1c}$ | |
| --- | --- | --- | --- | --- | --- | --- |
| Unit | mmol/l | (mg/dl) | mmol/l | (mg/dl) | mmol/mol | DCCT % |
| Normal | <7.8 | (<140) | <6.1 | (<110) | <42 | <6.0 |
| Impaired fasting glycaemia | <7.8 | (<140) | ≥6.1 <7.0 | (≥110) & (<126) | 42-46 | 6.0-6.4 |
| Impaired glucose tolerance | ≥7.8 | (≥140) | <7.0 | (<126) | 42-46 | 6.0-6.4 |
| Diabetes mellitus | ≥11.1 | (≥200) | ≥7.0 | (≥126) | ≥48 | ≥6.5 |

In one embodiment a "pre-diabetic subject" may be a subject presenting with a fasting serum glucose level of less than about 7.0 mmol/L. Suitably a pre-diabetic subject may be a subject presenting with a fasting serum glucose level of less than about 6.5 mmol/L.

In some embodiments a "pre-diabetic subject" may be a subject presenting with fasting serum glucose levels that are at the high end of the "normal" spectrum.

Thus in some embodiments a pre-diabetic subject may be a subject presenting with a fasting serum glucose level between about 4.25 to about 7.0 mmol/L, suitably about 4.5 to about 6.5 mmol/L, suitably about 5.0 to about 6.5 mmol/L. More suitably about 5.5 to about 6.5 mmol/L.

Use of the composition according to the present invention may result in a prevention of diabetes mellitus. In other words, the term "prevention" as used herein in reference to diabetes mellitus and/or a condition associated therewith means that the subject is less susceptible to diabetes mellitus (e.g. Type II diabetes mellitus) and/or a condition associated therewith as compared with a subject not administered with the compositions according to the present invention and/or that the subject is more able to counter or overcome the diabetes mellitus (e.g. Type II diabetes mellitus) and/or a condition associated therewith as compared with a subject not administered with the compositions according to the present invention.

In some embodiments the term "prevention" as used herein means the reversal of symptoms of diabetes mellitus and/or a condition associated therewith in a subject. Suitably "prevention" may mean that the fasting serum glucose level of a subject returns to a normal level following administration of the composition.

The term "normal level" as used in this context refers to a fasting serum glucose level in the range of between about 3.5 to about 6.1 mmol/L. Suitably a range between about 3.5 to about 5.0 mmol/L, more suitably a range between about 3.5 to about 4.5 mmol/L.

In embodiments of the invention where the composition is used for treating diabetes mellitus the composition may be administered to a subject having symptoms of and/or diagnosed as suffering from diabetes mellitus.

Suitably the subject may be a subject suffering from Type II diabetes mellitus.

The term "treating" used in the context of a subject suffering from diabetes mellitus (e.g. Type II diabetes mellitus) and/or a condition associated therewith may mean administering the composition for the purpose of "controlling" the diabetes mellitus (e.g. Type II diabetes mellitus) and/or a condition associated therewith.

For instance the term "treatment" and/or "treating" as used herein may be palliative or prophylactic. In other words when administered the composition, a subject may not be completely cured of the diabetes mellitus (e.g. Type II diabetes mellitus) and/or a condition associated therewith, but the diabetes mellitus (e.g. Type II diabetes mellitus) and/or a condition associated therewith may be in remission.

In some embodiments the term "treatment" and/or "treating" means that the diabetes mellitus (e.g. Type II diabetes mellitus) and/or a condition associated therewith is controlled.

An individual suffering from diabetes may be an individual having a fasting serum glucose level of greater than or equal to 7.1 mmol/L.

Advantages

The compositions for use, methods and/or uses according to the present invention achieve a number of distinct advantages. At least some of the advantages are discussed below.

It is a seminal finding of the inventors that a composition for use and/or a method according to the present invention allows for the administration of a low dosage of glucoraphanin. It is highly surprising that intermittently administering a composition of the invention to a subject between about 1 to about 5 times per week such that a subject is administered with a weekly dose of between about 300 to about 2500 μmoles of glucoraphanin is able to reduce fasting serum glucose levels and/or prevent and/or treat diabetes mellitus and/or a condition associated therewith. This is especially surprising when there is no disclosure in the art that glucoraphanin could achieve such advantageous technical effects.

Use of low dosages of glucoraphanin may have profound economic advantages e.g. where the composition for use comprises isolated and/or purified glucoraphanin.

It is highly advantageous to administer a composition (e.g. comprising glucoraphanin) according to the invention to a subject between about 1 to about 5 times per week such that a subject is administered with a weekly dose of between about 300 to about 2500 μmoles of glucoraphanin, as using a composition comprising glucoraphanin is more efficacious at reducing fasting serum glucose levels and/or preventing and/or treating diabetes mellitus and/or a condition associated therewith. For example, using such a composition is more advantageous than using a composition comprising a derivative of glucoraphanin (e.g. sulforaphane).

Sulforaphane is believed to be an active compound in cruciferous vegetables, especially those enriched in glucosinolates and/or derivatives thereof. However, without wishing to be bound by theory it is believed that less than 10% of glucoraphanin is converted to sulforaphane. Therefore it is even more surprising that using a low weekly dose of between about 300 to about 2500 μmoles of glucoraphanin could have such a striking effect on fasting serum glucose levels and/or the treatment and/or prevention of diabetes mellitus. Additionally or alternatively it is also advantageous to use a composition enriched in glucoraphanin over other glucosinolates or derivatives thereof such as sulforaphane as use of sulforaphane has been reported to have unwanted side-effects (e.g. gastrointestinal disturbances and/or discomfort and/or flatulence). Without wishing to be bound by theory this is expected to be especially true where high dosages of sulforaphane are administered to a subject.

The inventors surprisingly found that administering a substance with a composition of the invention between about 1 to about 5 times per week (preferably once or twice per week) may increase and/or improve the effect on the reduction of fasting serum glucose levels and/or prevention of and/or treatment of diabetes mellitus and/or a condition associated therewith.

Without wishing to be bound by theory the inventors believe that significantly better results can be achieved by intermittent administration when compared to continuous administration. It is believed that providing a "pulse" of glucoraphanin is more beneficial for reducing fasting serum glucose levels in a subject and/or preventing diabetes mellitus and/or a condition associated therewith and/or treating diabetes mellitus and/or a condition associated therewith. It is further believed that by continually administering a subject with glucoraphanin or a derivative of glucoraphanin (such as sulforaphane) that the metabolism and/or physiology of the subject adapts to the continuous presence of glucoraphanin and/or derivative thereof and that this results in a reduction in the effectiveness of the composition for use in the invention.

The inventors have found that intermittent administration as per the invention results in a "pulse" of glucoraphanin, which triggers metabolic changes in a subject administered with the composition. Advantageously, it is believed that due to intermittent administration and the "pulse" effect observed that only a low dose of glucoraphanin needs to be administered to a subject to reduce fasting serum glucose levels in a subject and/or prevent diabetes mellitus and/or a condition associated therewith and/or treat diabetes mellitus and/or a condition associated therewith.

Lower dosages of glucoraphanin will also reduce the risk of any side-effects associated with the administration thereof.

Furthermore, use of low dosages administered intermittently (e.g. about 1 to about 5 times per week, preferably once or twice per week) may allow for a more cost effective and/or efficient dosage regimen when compared to continual administration. For continual administration such as daily administration, it may be necessary to provide a greater amount of the composition of the invention leading to greater manufacturing costs and/or costs per patient and/or reduced efficiency and/or wastage.

Additionally, intermittent dosing (e.g. once or twice per week) according to the present invention may encourage patient compliance. Increased compliance may result in a more efficient and/or effective reduction of fasting serum glucose levels and/or prevention of and/or treatment of diabetes mellitus and/or a condition associated therewith.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

Amino acids are referred to herein using the name of the amino acid, the three letter abbreviation or the single letter abbreviation.

The term "protein", as used herein, includes proteins, polypeptides, and peptides.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "a composition" includes a plurality of such candidate agents and reference to "the composition" includes reference to one or more compositions and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

The invention will now be described, by way of example only, with reference to the following Figures and Examples.

EXAMPLES

Example 1

Materials & Methods

Sample

The study involves 100 patients aged 18-80 years with low- and intermediate-risk prostate cancer on active surveillance.

Volunteers are randomized to 1 of 3 treatment arms:

Arm I one portion (300 g each) per week of a soup containing standard broccoli

Arm II one portion (300 g each) per week of a soup containing glucoraphanin-enriched broccoli (Beneforte®)

Arm III one portion (300 g each) per week of a soup containing Beneforte extra broccoli The randomization is undertaken by a third party with the use of an electronic randomization generator (www.randomization.com). This uses a method called "Block randomisation" whereby volunteers are equally distributed to the three study arms.

Collection of blood and urine samples occurs at baseline and at 12 months after the dietary intervention. All study samples are used for global gene and metabolite analyses. Dietary and physical activity assessment occurs before starting the intervention, at six months and again one week before the end of the 12 month intervention period.

Recruitment Policy

Recruitment will continue until 78 volunteers have completed the study. It is anticipated that the dropout rate for this study is approximately 25% due to the clinical progression of prostate cancer within the 12-month study period; the study team will recruit up to 100 patients in order to allow for an approximately 25% dropout rate. Patients with low- and intermediate-risk prostate cancer on active surveillance, aged 18-80 years with a BMI between 19.5 and 35 kg/m2 are identified and recruited by Mr Robert Mills (consultant urologist) or Mr Omar Al Kadhi (research registrar) at the NNUH.

Screening Criteria

Basic Inclusion Criteria
Males 10
Diagnosed with low and intermediate prostate cancer risk on active surveillance
Aged 18-80 years
BMI between 19.5 and 35 kg/m2
Smokers and non-smokers
Basic Exclusion Criteria
Those undergoing chemopreventive therapy
Those regularly taking 5α-reductase inhibitors or testosterone replacement medicines
Those on warfarin treatment
Those diagnosed with diabetes
Those diagnosed with or suspected to be high-risk for human immunodeficiency virus (HIV) and/or hepatitis
Those allergic to any of the ingredients of the broccoli soups
Those taking dietary supplements or herbal remedies which may affect the study outcome—unless the volunteer is willing to discontinue taking them for 1 month prior to starting study. Please note that some supplements may not affect the study and this is assessed on an individual basis
Parallel participation in another research project that involves dietary intervention
Any person related to or living with any member of the study team Study Procedure This study will involve 78 volunteers aged between 18-80 years who will undertake the study as described below.

Dietary Assessment

We wish to measure the habitual diet in each of the groups as participants may already consume high levels of cruciferous vegetables as part of their normal diet. Once the participant is eligible to take part in the intervention, they are sent their first diary, which will need to be completed before they start eating the study soups. Volunteers are asked to complete an IFR standard 7-day food diary of estimated intake including dietary supplements or herbal treatments. Volunteers are instructed to record their intake of food, beverages and supplements consumed over a 7-day period (incorporating 7 different days, including weekends) using household measures as an indication of portion size. Details of how to complete the diary are given in annex 8 along with an example diary. After 6 months and one week before the end of the 12 month dietary intervention, a 2nd and 3rd 7-day diet diary will again be completed to assess compliance to the intervention. The food intake diaries are analysed using Diet Cruncher' or similar programs as well as UK food composition tables. We are also developing an additional food diary that will help us to specifically keep a record and provide details of foods regularly eaten (e.g. cruciferous vegetables, tomatoes, red meat, milk and dairy products) that are associated with risk of prostate cancer within some epidemiological studies (but not others), and so may be relevant for the interpretation of data.

Volunteers are asked to eliminate all cruciferous vegetables and other foods containing ITC precursors from their diet for 2 days prior to Visit 3. The volunteer is reminded of the list of foods to be avoided and if necessary, a photocopy of that page is given to the volunteer again. Based on previous studies, by avoiding food containing ITC precursors for at least 24 hours, we can ensure that ITCs will not be found in circulation (Gasper, A. V., et al., Glutathione S-transferase M1 polymorphism and metabolism of sulforaphane from standard and high-glucosinolate broccoli. Am J Clin Nutr, 2005. 82(6): p. 1283-91, which is incorporated herein by reference).

Blood Collection

The study nurse collects a blood sample (38 ml) from an appropriate vein in the volunteer's arm using a butterfly needle after assessing the condition of the volunteer's veins. The blood is used to measure fasting blood glucose and to measure glycated haemoglobin (HbA1c). The blood is mixed with an anti-coagulant (EDTA) and aliquoted and placed on dry ice until they can be safely transported back to the IFR to be stored at −80° C. until required.

Whole blood samples for a quantitative in vitro determination of Haemoglobin A1c concentration (HbA1c) are used. HbA1c is an indicator of the mean daily blood glucose concentration over the preceding 6-8 weeks. The analysis is carried out at the Institute of Food Research by using a latex enhanced immunoturbidimetric assay suitable for use on RX Daytona analyser. As an example the commercial kit supplied from RANDOX, Cat. No. HA3830 is capable of determining total haemoglobin and HbA1c within a sample and is suitable for use in conjunction with the RX Daytona analyser.

In addition, fasting glucose concentration is determined using the glucose assay Ref:3L82-20 and 3L82-40 supplied by Abbott CLINICAL CHEMISTRY.

Study Diet

Volunteers are randomly allocated to one of three dietary groups in which they are required to consume one portion of broccoli soup per week as part of their normal diet for one year. The three types of soup will contain standard broccoli—$Myb28^{villosa}$ null (i), glucoraphanin-enriched broccoli (Beneforte®)—$Myb28^{villosa}$ heterozygous (ii), or Beneforte extra broccoli ($Myb28^{villosa}$ homozygous) (iii) (see FIG. 4 and FIG. 6 which details the glucoraphanin in each of the broccoli types and glucoraphanin and sulphur content in the processed soups respectively).

Beneforte® and Beneforte extra have been developed by conventional breeding. Standard broccoli, Beneforte and Beneforte extra all have the same appearance and flavour thus enabling a double-blinded human intervention study to be undertaken.

Supply of Broccoli Soups

The three types of broccoli soups are prepared by Bakkavor, a leading international producer of fresh prepared foods. For each of standard, Beneforte® and Beneforte extra broccoli soups we will have three recipes (+sweet potato, +cheesy leek, +stilton). Ingredient declarations, nutritional information and allergy statements for the three broccoli soups have been provided from the producer. To improve study compliance, volunteers are able to choose between the three recipes. Bakkavor will make frozen soups and then arrange to be delivered to IFR (FIG. 5). Once delivered to IFR, soups are stored in a dedicated freezer at IFR HNU. Volunteers are informed on how to consume the soups by reading the participant information sheet, in brief the subject is instructed to thaw and heat up the soups prior to ingestion.

The ingredients for the broccoli soup are as follows: water, broccoli (28%), fresh milk, single cream, diced onion potato, stilton cheese (4%), cornflour, rapeseed oil, salt, black pepper.

The broccoli (28%) was selected from standard broccoli, Beneforte® broccoli or Beneforte Extra broccoli.

Monitoring of Diet and Compliance

Volunteers are asked to fill in a dietary record sheet during the 12-month intervention period, recording each time they eat their soups. This is intended to aid compliance with the dietary interventions and also to be used in comparison with the 7-day diet diary. Volunteers are telephoned by a member of the study team to monitor progress; the record sheet is collected and empty soup containers are counted by a member of the study team in parallel with the delivery of frozen soups.

We appreciate that volunteers may wish to go on holiday during the intervention period. Volunteers are allowed to go on holiday during the course of the intervention, provided they are able to incorporate the broccoli soups that would have been consumed during those days prior to and following their trip. We will ask the volunteers to inform us of any planned holiday dates so that we can keep a record and alter their clinical study days accordingly.

Statistical Analysis

Sample Size Calculation

It has been estimated that 26 subjects in each of the three dietary groups (78 in total) are required to detect 1.5 fold differences with a significant difference ($p<0.02$) between any two of the three dietary groups, with a power of 80% and a standard deviation of 0.66 (based on a log 2 scale of gene intensity measurements).

Data Analysis

The statistical analysis for data generated form this study is performed by using different methods.

Results

Fasting glucose data was obtained for subjects administered with a soup prepared with Beneforte Extra Broccoli as described in the Material and Methods section above.

FIG. 7 shows the results for one individual where it is clear that fasting blood glucose levels dropped drastically upon beginning administration with the Beneforte Extra Broccoli soup (Diet B).

FIG. 8 shows a statistical analysis of fasting serum glucose levels of individuals before administration with Beneforte Extra Broccoli soup, after 3 months and after 6 months. A clear reduction in fasting serum glucose levels can be observed with administration of 300 ml once per week.

TABLE 1

Mean glucose levels at baseline, 3 and 6 months related to the data in FIG. 8.

|  | Baseline | 3 months | 6 months |
|---|---|---|---|
| Mean | 5.450 | 5.043 | 4.740 |
| Std. Deviation | 0.4973 | 0.6294 | 0.1342 |
| Lower 95% CI of mean | 5.163 | 4.461 | 4.573 |
| Upper 95% CI of mean | 5.737 | 5.625 | 4.907 |
| P value (two tailed) |  | 0.1840 | 0.0004 |

TABLE 2

Mean glucose levels at baseline, 3 and 6 months related to the data in FIG. 9.

|  | Baseline | 3 months | 6 months |
|---|---|---|---|
| Mean | 1.000 | 0.9350 | 0.8588 |
| Std. Deviation | 0.0 | 0.07044 | 0.06330 |
| Lower 95% CI of mean | 1.000 | 0.8698 | 0.7802 |
| Upper 95% CI of mean | 1.000 | 1.000 | 0.9374 |
| P value (two tailed) |  | 0.0504 | 0.0076 |

Example 2

Materials & Methods

40 Volunteers are randomized to 1 of 2 treatment arms:
Arm 1 one portion (300 g each) per week of a soup containing standard broccoli (Myb28$^{villosa}$ null)
Arm 2 one portion (300 g each) per week of a soup containing Beneforte extra broccoli (Myb28$^{villosa}$ homozygous)

The randomization can be undertaken by a third party with the use of an electronic randomization generator (www.randomization.com). This uses a method called "Block randomisation" whereby volunteers are equally distributed to the two study arms.

Blood samples are collected at baseline and at 3 monthly intervals until 24 months.

Inclusion Criteria

Males
Aged 35-85 years
BMI between 20 and 32 kg/m2

Exclusion Criteria

Those undergoing chemopreventive therapy
Those diagnosed with diabetes and/or taking medications that can be used to treat diabetes
Those diagnosed with or suspected to be high-risk for human immunodeficiency virus (HIV) and/or hepatitis
Those allergic to any of the ingredients of the broccoli soups
Those taking dietary supplements or herbal remedies which may affect the study outcome—unless the volunteer is willing to discontinue taking them for 1 month prior to starting study. Please note that some supplements may not affect the study and this is assessed on an individual basis
Parallel participation in another research project that involves dietary intervention
Any person related to or living with any member of the study team

Study Procedure

This study involves 40 volunteers aged between 35-85 years. The study undertaken is described below.

Volunteers are asked to maintain their normal diet and not deviate during the study.

Blood collection: The study nurse takes a blood sample (38 ml) from an appropriate vein in the volunteer's arm using a butterfly needle after assessing the condition of the volunteer's veins. The blood is used to measure fasting blood glucose. The blood is mixed with an anti-coagulant (EDTA) and aliquoted and placed on dry ice until they can be safely stored at −80° C. until required. Fasting glucose concentration is determined using the glucose assay Ref: 3L82-20 and 3L82-40 supplied by Abbott Clinical Chemistry.

Study Diet

Volunteers are randomly allocated to one of two dietary groups in which they are required to consume one 300 ml portion of broccoli soup per week as part of their normal diet for six months. The two types of soup will contain standard broccoli—Myb28$^{villosa}$ null, or Beneforte extra broccoli (Myb28$^{villosa}$ homozygous). The Beneforte extra broccoli provided about 450 μmol of glucoraphanin per 300 ml portion. The control (standard broccoli) provided less than 100 μmol of glucoraphanin per 300 ml portion. Beneforte extra have been developed by conventional breeding. Standard broccoli and Beneforte extra all have the same appearance and flavour thus enabling a double-blinded human intervention study to be undertaken.

Supply of Broccoli Soups

The two types of broccoli soups are prepared by Bakkavor, a leading international producer of fresh prepared foods. Frozen soups are stored in a dedicated freeze. Volunteers are informed on how to consume the soups; in brief the subject is instructed to thaw and heat up the soups prior to ingestion. The ingredients for the broccoli soups are as follows: water, broccoli (28%), fresh milk, single cream, diced onion potato, stilton cheese (4%), cornflour, rapeseed oil, salt, black pepper. The broccoli (28%) was selected from standard broccoli or Beneforte Extra broccoli.

Monitoring of Compliance

Subjects are asked to maintain a subject diary wherein the subject is requested to complete daily and to record their consumption of the test product. Volunteers are allowed to go on holiday during the course of the intervention, provided they are able to incorporate the broccoli soups that would have been consumed during those days prior to and following their trip. We will ask the volunteers to inform us of any planned holiday dates so that we can keep a record and alter their clinical study days accordingly.

Results

Fasting blood glucose is represented as fold change from base line. Statistical analyses are by paired T-tests.

For Beneforte Extra soup (arm 2, FIG. 10), fasting blood glucose falls by 10% after three months and then remains approximately 10% below baseline for the subsequent 21 months. At each three month time point the fall is significantly different from baseline, with the exception of the 12 month time point at which there is considerable variation between individuals. This may be due to a single non fasted blood sample that causes a statistical anomaly.

For standard broccoli soup (arm 1, FIG. 11) there is a reduction in mean fasted blood glucose after three months, but this is not significantly different from baseline (P>0.05). For the subsequently 21 months, there are no significantly difference from baseline except for samples at 9 months that were 5% reduction from base line (P<0.05).

We conclude that consuming one 300 ml portion of soup containing Beneforte Extra soup results in a significantly and sustained reduction in fasted blood glucose level, whereas consuming soup with standard broccoli does not result in a reduction in fasted blood glucose.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A method of: reducing fasting serum glucose levels in a subject having elevated fasting serum glucose levels; treating a subject having diabetes mellitus and/or a condition associated therewith; or combinations thereof, comprising intermittently administering to a subject a composition comprising:
   a. glucoraphanin; and/or
   b. a composition prepared from a high glucosinolate Cruciferous vegetable, portion thereof or extract thereof;
   wherein said composition is intermittently administered to the subject between about 1 to about 5 times per week such that said subject is administered with a weekly dose of between about 300 to about 2500 µmoles of glucoraphanin.

2. A method according to claim 1, wherein the composition comprising glucoraphanin is prepared from a high glucosinolate Cruciferous vegetable, portion thereof or extract thereof.

3. A method according to claim 1, wherein the high glucosinolate Cruciferous vegetable, portion thereof or extract thereof is a broccoli plant, portion thereof or extract thereof.

4. A method according claim 1, wherein the composition is intermittently administered to the subject between about 1 to about 3 times per week.

5. A method according to claim 1, wherein the composition is intermittently administered to the subject once per week.

6. A method according to claim 1, wherein the composition is intermittently administered to the subject such that said subject is administered with a weekly dose of between about 350 to about 500 µmoles of glucoraphanin.

7. A method according to claim 6, wherein the composition is intermittently administered to the subject such that said subject is administered with a weekly dose of between about 350 to about 480 µmoles of glucoraphanin.

8. A method according to claim 1, wherein the subject is a pre-diabetic subject.

9. A method according to claim 1, wherein the composition is formulated as a foodstuff, a vegetable extract and/or a pharmaceutical composition.

10. A method according to claim 9, wherein said foodstuff is a prepared food product.

11. A method according to claim 10, wherein the prepared food product is a soup.

12. A method according to claim 3, wherein the high glucosinolate Cruciferous vegetable portion thereof or extract thereof and/or broccoli plant, portion thereof or extract thereof comprises SEQ ID No. 1 except for at least one polymorphism selected from the group consisting of:
   a. a single nucleotide polymorphism (SNP) at a position corresponding to nucleotide 83, 136, 226, 563, 610, 830, 995, 1116, 1513, 1577, 1606, 1620, 1825, 1863, 1877 or 2026 of SEQ ID NO: 1; or
   b. a polymorphism in the number of nucleotides present between nucleotides 323 and 332, between nucleotides 521 and 524, between nucleotides 783 and 786, between nucleotides and 909 and 914, between nucleotides 1365 and 1369, between 1811 and 1821, or between nucleotides 2046 and 2056 of SEQ ID NO: 1; or
   c. a polymorphism in the number of nucleotides present between nucleotides 836 and 837, between nucleotides 867 and 868, or between nucleotides 943 and 944 of SEQ ID NO: 1.

13. A method according claim 3, wherein the high glucosinolate Cruciferous vegetable portion thereof or extract thereof and/or broccoli plant, portion thereof or extract thereof comprises SEQ ID NO: 2 or a sequence which has a least 97% identity with SEQ ID NO: 2.

14. A method according to claim 3, wherein the high glucosinolate broccoli plant, portion thereof or extract thereof is a Myb28Villosoa high glucosinolate broccoli plant, portion thereof or extract thereof.

* * * * *

UNITED STATES PATENT AND TRADEMARK OFFICE
CERTIFICATE OF CORRECTION

PATENT NO. : 11,147,825 B2
APPLICATION NO. : 15/738660
DATED : October 19, 2021
INVENTOR(S) : Richard Mithen It is certified that error appears in the above-identified patent and that said Letters Patent is hereby corrected as shown below:

On the Title Page

Item (54) and in the Specification, Column 1, Lines 1-3, "GLUCORAPHNIN" should be -- GLUCORAPHANIN --.

In the Claims

At Column 37, Lines 19-20, "glucosinolate Cruciferous" should be -- glucosinolate cruciferous --.

At Column 37, Line 30, "glucosinolate Cruciferous" should be -- glucosinolate cruciferous --.

At Column 37, Line 33, "glucosinolate Cruciferous" should be -- glucosinolate cruciferous --.

At Column 37, Line 36, "according claim" should be -- according to claim --.

At Column 38, Line 20, "glucosinolate Cruciferous" should be -- glucosinolate cruciferous --.

At Column 38, Line 39, "according claim" should be -- according to claim --.

At Column 38, Lines 39-40, "glucosinolate Cruciferous" should be -- glucosinolate cruciferous --.

At Column 38, Line 46, "Myb28Villosoa" should be -- $Myb28^{Villosoa}$ --.

Signed and Sealed this
Thirtieth Day of August, 2022

Katherine Kelly Vidal
*Director of the United States Patent and Trademark Office*

SEQUENCE LISTING

<160> NUMBER OF SEQ ID NOS: 2

<210> SEQ ID NO 1
<211> LENGTH: 2186
<212> TYPE: DNA
<213> ORGANISM: Brassica oleracea

<400> SEQUENCE: 1

| | | | | | |
|---|---|---|---|---|---|
| gaaaatcaca | gttcacgcct | cttactccat | gagcttctct | attctcatcc | tagtgttata | 60 |
| atcttgcaaa | cacatataga | aagcaaggtt | tggagtgtac | gagaaaaaca | tgaaaacacc | 120 |
| tagaagctct | gtgggtgaga | cccaagagcg | tttctcgatt | agtttcatat | acagatgcat | 180 |
| cagagttctc | atcaaccgat | ctacttcttt | cttatcttat | tagaagaaaa | aaatcctatc | 240 |
| aaaatttact | ttcctgcaag | tatattttc | tttacatttt | cattttcttg | agtgttattt | 300 |
| gagtgaagtt | atattaaaat | attgtaatag | agttcatata | tatcgaaaat | gtcaagaaag | 360 |
| ccatgttgtg | tcggagaagg | gctgaagaaa | ggggcatgga | ccaccgagga | agataagaaa | 420 |
| ctcatctctt | acatccatga | acatggagaa | ggaggctggc | gcgacattcc | tcaaaaagct | 480 |
| ggttaatatc | tattatatat | tttttggtaa | attttaaaa | catatatatg | tttgtttggt | 540 |
| atttgatgta | tgaaagtttt | atgttgaata | tggtgtttta | ctaggrttga | aaaggtgtgg | 600 |
| aaagagttgt | agactgcgat | ggactaacta | cctaaaacct | gagatcaaaa | gaggcgagtt | 660 |
| tagttcagag | gaggaacaga | ttatcatcat | gctccatgct | gctcgtggca | acaagtacgt | 720 |
| ttattttaga | ccaaaaaaaa | acaagtacgt | ttatttttaa | caaaaaggac | gattatatat | 780 |
| ttttatgtgt | gtatggatcc | tccagtgatc | atcattctag | ttttctcttt | tttttatac | 840 |
| cgcaaacaaa | tttcattagt | aaaaaaatta | aaattccaaa | gtcaatattc | aaaaacacag | 900 |
| tgttatatat | ataatcctat | atatgtcata | tattaaaaaa | gtacaacatg | agaaatgaat | 960 |
| ttaagtatgc | ttctaaagcg | aagttttact | tcccgaaaaa | ttattcttta | tttttttcat | 1020 |
| gtatttgaca | attctctgat | gcaaaatatg | tgtttgatta | gcaatatgtg | actaaaaatt | 1080 |
| gcaatagcac | acatcatttt | agtctctatt | ccataaaaaa | gcttcaaaat | aaatttgatt | 1140 |
| aactttggtc | ttccatctta | tctctttcac | tattcttgtc | tttaggtggt | cggtcatagc | 1200 |
| kagacattta | cctagaagaa | cmgacaatga | gatcaagaac | tactggaaca | cacatctcaa | 1260 |
| gaaacgtttg | atcgaacagg | gtactgatcc | cgtgactcac | aagccactag | cttctaatac | 1320 |
| aaaccctact | gtacctgaga | atttgcattc | cctagatgca | tctagtaatt | ccgacaagca | 1380 |
| atactcccgg | tcaagctcaa | tgccttccat | gtcttgtact | ccttcctccg | gtttcaacac | 1440 |
| ggttttcgag | aataccagca | aagatgggac | accagttcgt | gaggacgatt | ccttgagtcg | 1500 |
| caagaaacgt | tttaagaaat | caagttctac | atcaaggctt | ttgaacaaag | ttgcggctaa | 1560 |
| ggccacttcc | atgaaagaag | ctttgtctgc | ttccatggaa | ggtagtttga | atgctaatac | 1620 |
| aagcttttcc | aatggctact | ctgagcagat | tctcaatgaa | gatgatagtt | ctaatgcatc | 1680 |
| cctcataaac | actctcgccg | agttcgatcc | cttcctccaa | acaacgtttt | accctgagaa | 1740 |
| tgagatgaat | actacttctg | atctcggtat | agatcaggac | tacttctcac | attttctcga | 1800 |
| aaatttcggc | agagatgatg | accacaatga | ggagcactac | atgaatcata | actatggtca | 1860 |
| tgatcttctt | atgtccgatg | tgtcccaaga | agtctcatca | actagcgttg | atgatcaaga | 1920 |
| caatactaat | gagggttggt | caaattatct | tcttgaccat | gctgatttta | tacatgacat | 1980 |
| ggattctgat | tccctcggaa | agcatctcat | atgaatcttc | gtgcccaagc | agaaaggttt | 2040 |
| caaacttttg | aaacttgtca | gaacaagaag | ttatgtatgt | attctattat | atggattgtt | 2100 |

| | | | | |
|---|---|---|---|---|
| tagtatatgt | ccaagatcat | ggttgttagt | cccaagttta | gggtttgtat | aatatacaat | 2160 |
| aagggacgtt | atcttataaa | acgagg | | | | 2186 |

<210> SEQ ID NO 2
<211> LENGTH: 2165
<212> TYPE: DNA
<213> ORGANISM: Brassica villosa

<400> SEQUENCE: 2

| | | | | | |
|---|---|---|---|---|---|
| gaaaatcaca | gttcacgcct | cttactccat | gagcttctct | attctcatcc | tagtgttata |  60 |
| atcttgcaaa | cacatataga | aagcaagatt | tggagtgtac | gagaaaaaca | tgaaaacacc | 120 |
| tagaagctct | gtgggtaaga | cccaagagcg | tttctcgatt | agtttcatat | acagatgcat | 180 |
| cagagttctc | atcaaccgat | ctacttcttt | cttatcttat | tagaaaaaaa | aaatcctatc | 240 |
| aaaatttact | ttcctgcaag | tatatttttc | tttacatttt | cattttcttg | agtgttattt | 300 |
| gagtgaagtt | atattaaaat | attgttcata | tatatcgaaa | atgtcaagaa | agccatgttg | 360 |
| tgtcggagaa | gggctgaaga | aagggcatg | gaccaccgag | aagataaga | aactcatctc | 420 |
| ttacatccat | gaacatggag | aaggaggctg | gcgcgacatt | cctcaaaaag | ctggttaata | 480 |
| tctattatat | attttttggt | aaattttaa | acatatatg | tttgtttggt | atttgatgta | 540 |
| tgaaagtttt | atattgaatg | tggtgtttta | ctaggattga | aaaggtgtgg | aaagagttgc | 600 |
| agactgcgat | ggactaacta | cctaaaaacct | gagatcaaaa | gaggcgagtt | tagttcagag | 660 |
| gaggaacaga | ttatcatcat | gctccatgct | gctcgtggca | acaagtacgt | ttattttaga | 720 |
| ccaaaaaaaa | acaagtacgt | ttattttaa | caaaaaggac | gattatatat | ttttgtgtgt | 780 |
| atggatcctc | cagtgatcat | cattctagtt | ttctcttctt | tttttatac | cgcaaacaaa | 840 |
| tttcattagt | aaaaaaaatt | aaaattccaa | agtcaatatt | caaaaacaca | gtgttatata | 900 |
| atcctatata | tgtcatatat | taaaaaagta | tattaaaaaa | gtacaacatg | agaaatgaat | 960 |
| ttaagtatgc | ttctaaagcg | aagttttact | tcccaaaaaa | ttattctta | tttttttcat | 1020 |
| gtatttgaca | attctctgat | gcaaaatatg | tgtttgatta | gcaatatgtg | actaaaaatt | 1080 |
| gcaatagcac | acatcatttt | agtctctatt | ccatagaaaa | gcttcaaaat | aaatttgatt | 1140 |
| aacttggtc | ttccatctta | tctctttcac | tattcttgtc | tttaggtggt | cggtcatagc | 1200 |
| kagacattta | cctagaagaa | cmgacaatga | gatcaagaay | tactggaaca | cacatctcaa | 1260 |
| gaaacgtttg | atcgaacagg | gtactgatcc | cgtgactcac | aagccactag | cttctaatac | 1320 |
| aaaccctact | gtacctgaga | atttgcattc | cctagatgca | tctagttccg | acaagcaata | 1380 |
| ctcccggtca | agctcaatgc | cttccatgtc | ttgtactcct | tcctccggtt | tcaacacggt | 1440 |
| tttcgagaat | accagcaaag | atgggacacc | agttcgtgag | gacgattcct | tgagtcgcaa | 1500 |
| gaaacgtttg | aagaaatcaa | gttctacatc | aaggcttttg | aacaaagttg | cggctaaggc | 1560 |
| cacttccatg | aaaaaagctt | tgtctgcttc | catggaaggt | agcttgaatg | ctaatataag | 1620 |
| ctttcccaat | ggctactctg | agcagattct | caatgaagat | gatagttcta | atgcatccct | 1680 |
| cataaacact | ctcgccgagt | tcgatcccctt | cctccaaaca | acgttttacc | ctgagaatga | 1740 |
| gatgaatact | acttctgatc | tcggtataga | tcaggactac | ttctcacatt | ttctcgaaaa | 1800 |
| tttcggcaac | cataatgagg | agcactacat | gaatcataac | tatggtcatg | gtcttcttat | 1860 |
| gtcctatgtg | tccaagaag | tctcatcaac | tagcgttgat | gatcaagaca | atactaatga | 1920 |
| gggttggtca | aattatcttc | ttgaccatgc | tgattttata | catgacatgg | attctgattc | 1980 |

```
cctcggaaag catctcatat gaatcttcgt gcctaagcag aaaggtttca aacttgtcag    2040
aacaagaagt tatgtatgta ttctattata tggattgttt agtatatgtc caagatcatg    2100
gttgttagtc ccaagtttag ggtttgtata atatacaata agggacgtta tcttataaaa    2160
cgagg                                                                2165
```